US007465699B2

(12) United States Patent
Trinh et al.

(10) Patent No.: US 7,465,699 B2
(45) Date of Patent: Dec. 16, 2008

(54) FABRIC SOFTENING COMPOSITIONS AND METHODS

(75) Inventors: Toan Trinh, Maineville, OH (US); Eva Schneiderman, Fairfield, OH (US); David Thomas Stanton, Hamilton, OH (US); John William Smith, Milford, OH (US); Michael Lee Kramer, Cincinnati, OH (US); Helen Bernardo Tordil, Fairfield, OH (US); Gayle Marie Frankenbach, Cincinnati, OH (US); Zaiyou Liu, West Chester, OH (US); Mary Vijayarani Barnabas, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/819,069

(22) Filed: Apr. 6, 2004

(65) Prior Publication Data
US 2004/0235706 A1 Nov. 25, 2004

Related U.S. Application Data

(62) Division of application No. 09/989,640, filed on Nov. 20, 2001, now Pat. No. 6,815,411.

(60) Provisional application No. 60/252,342, filed on Nov. 20, 2000.

(51) Int. Cl.
*C11D 3/37* (2006.01)
(52) U.S. Cl. .............................. 510/466; 51/522; 51/527
(58) Field of Classification Search ................. 510/421, 510/466, 524, 527, 522
See application file for complete search history.

(56) References Cited

U.S. PATENT DOCUMENTS 3,299,112 A 1/1967 Bailey
3,402,192 A * 9/1968 Haluska ....................... 556/437
4,818,421 A * 4/1989 Boris et al. .................. 510/297
5,545,342 A * 8/1996 Beagle et al. ................ 510/299
5,880,089 A 3/1999 Lentsch et al.
5,942,217 A * 8/1999 Woo et al. .................. 424/76.1
5,955,093 A 9/1999 Woo et al.
6,001,343 A 12/1999 Trinh et al.
6,040,288 A 3/2000 Popoff et al.
6,315,800 B1 * 11/2001 Gomes et al. ................... 8/137

FOREIGN PATENT DOCUMENTS

| EP | 0 544 493 A | 6/1993 |
|---|---|---|
| EP | 0 841 391 | 5/1998 |
| EP | 1 092 803 A | 4/2001 |
| WO | WO 98/20098 A1 | 5/1998 |
| WO | WO 98/39401 | 9/1998 |
| WO | WO 99/41347 | 8/1999 |
| WO | WO 00/24857 A | 5/2000 |

OTHER PUBLICATIONS

OSI Specialities, Inc., Silwet Surfactants, Jun. 1994, Danbury, CT.

* cited by examiner

*Primary Examiner*—John R Hardee
(74) *Attorney, Agent, or Firm*—Mark A. Charles; David V. Upite; Kim William Zerby

(57) ABSTRACT

The present invention relates to stable, aqueous fabric softening compositions, fabric softening methods and articles of manufacture that use such fabric softening compositions comprising preferred polyalkyleneoxy polysiloxanes selected from the group consisting of polyethyleneoxy polysiloxane, polyethyleneoxy/polypropyleneoxy polysiloxanes, and mixtures thereof. The composition is preferably applied as small particle size droplets, especially from spray containers. The present invention also relates to a method of identifying, selecting, and/or designing the preferred polyethyleneoxy polysiloxanes and/or polyethyleneoxy/polypropyleneoxy polysiloxanes that provide superior fabric softening performance in general, and especially for use in the fabric softening composition of the present invention.

20 Claims, No Drawings

FABRIC SOFTENING COMPOSITIONS AND METHODS

CROSS REFERENCE TO RELATED APPLICATIONS

This application is a divisional of U.S. application Ser. No. 09/989,640, now U.S. Pat. No. 6,815,411 filed Nov. 20, 2001; and claims priority under 35 U.S.C. § 119(e) to U.S. Provisional Application Ser. No. 60/252,342, filed Nov. 20, 2000.

TECHNICAL FIELD

The present invention relates to stable, preferably translucent, more preferably clear, aqueous fabric softening compositions, articles of manufacture, and/or method of use, comprising selected polyalkyleneoxy polysiloxanes. This fabric softening composition is designed to be applied mainly on fabrics outside of the laundry processes, but can also be used during the laundry processes.

BACKGROUND OF THE INVENTION

Fabric softening benefit obtained in the home is traditionally provided during the laundry cycle, either by using a rinse-added fabric softener that is added to the rinse cycle, or a dryer-added fabric softener, most commonly a dryer-added sheet, to be added to the dryer. Traditional rinse-added and dryer-added fabric softener products typically are used to treat a whole load of fabrics in the laundry cycle, e.g., in a washer or an automatic dryer. However, it is usually inconvenient and/or wasteful to soften a single or a few clothing items with this method. This is a frequent and common problem, when only one or two fabric items need to be washed. In such cases, the fabrics are usually washed by hand and line dried. Included to this category are delicate fabrics that need to be hand washed individually, and not to be dried in an automatic clothes dryer. The hand-washed and line-dried fabric items usually feel coarse and harsh, unlike the items that are machine washed and/or dried in an automatic clothes dryer.

Most consumer rinse-added fabric softener and dryer-added fabric softener compositions contain dialkyl and/or alkenyl quaternary ammonium salts as the main fabric softening active. Examples of quaternary ammonium fabric softening actives are disclosed in U.S. Pat. No. 3,861,870, Edwards et al.; U.S. Pat. No. 4,308,151, Cambre; U.S. Pat. No. 3,886,075, Bernardino; U.S. Pat. No. 4,233,164, Davis; U.S. Pat. No. 4,401,578, Verbruggen; U.S. Pat. No. 3,974,076, Wiersema et al.; and U.S. Pat. No. 4,237,016, Rudkin et al. Some preferred quaternary ammonium fabric softening active systems are disclosed in U.S. Pat. No. 4,661,269, issued Apr. 28, 1987, to T. Trinh et al.; U.S. Pat. No. 5,545,340, issued Aug. 13, 1996, to Wahl et al.; U.S. Pat. No. 5,747,443 issued May 5, 1998 to E. H. Wahl et al.; and U.S. Pat. No. 5,830,845 issued Nov. 3, 1998 to T. Trinh et al. Examples of dryer-added fabric softener actives are given in U.S. Pat. No. 6,046,154 issued Apr. 4, 2000 to Trinh et al.; other dryer-added fabric softener actives can be found in U.S. Pat. Nos. 4,327,133; 4,421,792; 426,299; 4,460,485; 3,644,203; 4,661,269; 4,439,335; 3,861,870; 4,308,151; 3,886,075; 4,233,164; 4,401,578; 3,974,076; 4,237,016 and EP 472,17.

Alternative actives have been suggested, such as silicones, due to their lubricity. Silicones can be used in liquid fabric softener compositions to provide additional fabric feel, as is disclosed in U.S. Pat. No. 4,855,072 issued Aug. 8, 1989 to Trinh et al, said patent being incorporated herein by reference. The preferred silicones are polydimethylsiloxanes that can be incorporated into the softener compositions as a neat fluid, or can be added in a preemulsified form which is available from many suppliers. Examples of these preemulsified silicones are a 60% emulsion of polydimethylsiloxane (350 cs) from Dow Corning Corporation under the trade name DOW CORNING® 1157 Fluid, and a 50% emulsion of polydimethylsiloxane (10,000 cs) from General Electric Company under the trade name General Electric® SM 2140 Silicones. In order to increase fabric substantivity of the silicones to improve fabric feel, the silicones can be derivatised with cationic groups, such as those disclosed in U.S. Pat. No. 5,098,979 issued Mar. 24, 1992 and U.S. Pat. No. 5,196,499 issued Mar. 23, 1993, both to O'Lenick, Jr., or the silicones can be derivatised with reactive, curable groups that can condense to form higher molecular weight silicones, such as those disclosed in U.S. Pat. No. 4,419,391 issued Dec. 6, 1983 to Tanaka et al., all said patents are incorporated herein by reference.

It is well known that after treated several times with rinse-added fabric softener products and/or dryer-added fabric softener products, the cotton fabrics become somewhat waterproof, and become less water absorbent. This is because the common fabric softener actives are substantive to fabrics.

The silicones can also be derivatised with hydrophilic groups, to make them able to self-emulsify and/or to provide surface activity. The most common silicones of this class are the polyalkyleneoxy polysiloxanes. Commercial literature on polyalkyleneoxy polysiloxanes, such as "Silwet® Surfactants", OS-144 6/94-10M, published by OSi Specialties, Inc., discloses that some of the polyalkyleneoxy polysiloxanes add softness to fabrics, and that the softness property increases with the percent silicone in the polyalkyleneoxy polysiloxanes.

Although many of the fabric softener actives have been disclosed as having softening activity, there has been no characterization of which softener actives are most effective and/or preferred in the context of a product which is sprayed onto the fabrics as opposed to being deposited in the rinse and/or washing steps from a highly dilute aqueous bath. The art has not considered what is the optimum softener when there is no competition between the fabrics and the aqueous bath.

In one aspect the present invention relates to stable, preferably translucent, more preferably clear, aqueous fabric softening compositions comprising polyalkyleneoxy polysiloxanes which comprise at least some ethyleneoxy units, articles of manufacture comprising said compositions and/or method for use of said compositions on fabrics, preferably by direct application of said compositions on fabrics. Preferably, the compositions are used by the consumer to spray onto fabrics, particularly clothes, one at a time, to conveniently provide fabric softening benefit, without having to treat the whole load of fabrics in a washer and/or dryer, and/or without having to iron the fabrics. Cotton fabrics treated with the composition of the present invention do not become waterproof and synthetic fabrics can become more water absorbent. The articles of manufacture of the present invention preferably are packaged in association with instructions for use to direct the consumer to use the composition to treat fabrics correctly, including, e.g., the manner and/or amount of composition to spray, e.g., to apply an effective amount of the fabric softening composition and/or polyethyleneoxy polysiloxane to the fabric, to provide the fabric softening benefit, without the need of using the traditional rinse-added or dryer-added softener products and/or ironing. The fabric softening actives of the present invention can readily be washed off the fabrics. The aqueous fabric softening compositions of the present invention contain polyalkyleneoxy polysiloxanes as a key softening actives. However, it is found that in the context of the aqueous fabric softening compositions of the present invention, that are designed for direct application on fabrics, contrary to the teaching in the Silwet® Surfactants literature, the percent silicone alone correlates very poorly with the fabric softening performance of the spray compositions. Instead, it is discovered, using a quantitative structure-activity relationship (QSAR) approach, that the fabric softening performance of the compositions of the present invention depends on a combination of several properties of the polyalkyleneoxy polysiloxanes including the average total number of $SiMe_2O$ units in the molecule, the average total number of ethyleneoxy $CH_2CH_2O$ units in the molecule, and the % silicone.

The compositions of the present invention can provide other fabric care benefits, such as, wrinkle removal, wrinkle reduction, fabric color restoration, and/or fabric color rejuvenation, and when optional ingredients are present, the compositions can optionally provide other fabric care benefits, such as malodor control, static control, antibacterial action, insect repellency, and the like, as well as a "scent signal" in the form of a pleasant odor, and combinations thereof.

SUMMARY OF THE INVENTION

The present invention relates to stable, preferably translucent, more preferably clear, aqueous fabric softening compositions, fabric softening methods and articles of manufacture that use such fabric softening compositions, for use on fabrics, comprising:
(A) an effective amount to soften fabric of polyalkyleneoxy polysiloxane selected from the group consisting of polyethyleneoxy polysiloxane, polyethyleneoxy/polypropyleneoxy polysiloxanes, and mixtures thereof, having a molecular weight of from about 1,200 to about 200,000 and being characterized by Correlation I:

$$S = 3.246(\sqrt{t\#diSi}) - 1.880(\sqrt{\%Si}) - 0.9066\sqrt{t\#EO} + 17.70 \qquad (I)$$

wherein t#diSi is the average total number of the $Si(CH_3)_2O$ units in the molecule; % Si is the weight percent of total siloxane units in the molecule; t#EO is the average total number of the ethyleneoxy $CH_2CH_2O$ units in the molecule; and S is the Softness Index which is typically at least about 10;
(B) optionally, an effective amount of fabric wrinkle control agent;
(C) optionally, but preferably, an effective amount to provide olfactory effects of perfume;
(D) optionally, an effective amount to clarify the composition and/or improve the performance of the composition of surfactant;
(E) optionally, an effective amount, to kill, or reduce the growth of microbes, of antimicrobial active;
(F) optionally, an effective amount to assist in antimicrobial action of aminocarboxylate chelator;
(G) optionally, an effective amount to control malodor of odor controlling agent;
(H) optionally, an effective amount of antimicrobial preservative;
(I) optionally, an effective amount of adjunct quaternary ammonium fabric softening agent to provide additional fabric softening benefit; and
(J) aqueous carrier;

said composition preferably containing at least one of (B) through (I).

The present invention also relates to concentrated compositions, wherein the level of polyethyleneoxy polysiloxane is from about 1% to about 40%, preferably from about 2% to about 20%, more preferably from about 3% to about 10%, by weight of the composition which are diluted to form compositions with the usage concentrations of polyethyleneoxy polysiloxane of, e.g., from about 0.1% to about 5%, by weight of the diluted composition, as given hereinabove, which are the "usage conditions".

The present invention also relates to the compositions incorporated into a spray dispenser (sprayer) to create an article of manufacture that can facilitate treatment of fabric articles and/or surfaces with said compositions containing polyethyleneoxy polysiloxane and other optional ingredients at a level that is effective, yet is not discernible when dried on the surfaces. The spray dispenser comprises manually activated and non-manual operated spray means and a container containing the fabric softening composition. The articles of manufacture preferably are in association with instructions for use to direct the consumer to apply an effective amount of the fabric softening composition and/or polyethyleneoxy polysiloxane to the fabric to provide the desired benefit.

The present invention also comprises the use of small particle diameter droplets of the compositions herein, to treat fabrics, to provide superior performance, e.g., the method of applying the compositions to fabrics, etc. as small particles (droplets) preferably having average particle sizes (diameters) of from about 10 μm to about 120 μm, more preferably from about 20 μm to about 100 μm.

The present invention also relates to a method of using Correlation I to identify, select, and/or design the preferred polyethyleneoxy polysiloxanes and/or polyethyleneoxy/polypropyleneoxy polysiloxanes that provide superior fabric softening performance in general, and especially for use in the fabric softening composition of the present invention.

DETAILED DESCRIPTION OF THE INVENTION

The present invention relates to a stable, preferably translucent, more preferably clear, aqueous fabric softening composition, fabric softening methods and articles of manufacture that use such fabric softening composition, for use on fabrics, comprising:
(A) an effective amount to soften fabric, typically from about 0.01% to about 10%, preferably from about 0.1% to about 5%, more preferably from about 0.2% to about 3%, and even more preferably from about 0.3% to about 2%, by weight of the composition of polyalkyleneoxy polysiloxane selected from the group consisting of polyethyleneoxy polysiloxane, polyethyleneoxy/polypropyleneoxy polysiloxanes, and mixtures thereof, having a molecular weight of at least about 1,200, preferably from about 2,000 to about 200,000, more preferably from about 4,000 to about 150,000, even more preferably from about 5,000 to about 120,000, and yet more preferably from about 6,000 to about 100,000, and being characterized by Correlation I:

$$S = 3.246(\sqrt{t\#diSi}) - 1.880(\sqrt{\%Si}) - 0.9066\sqrt{t\#EO} + 17.70 \qquad (I)$$

wherein t#diSi is the average total number of the $Si(CH_3)_2O$ units in the molecule; % Si is the weight percent of total silicone (or siloxane) in the molecule; t#EO is the average total number of the ethyleneoxy $CH_2CH_2O$ units in the molecule; and S is the Softness Index which is typically at least about 10, preferably at least about 15, more preferably at least about 20, even more preferably at least about 25, yet more preferably at least about 30; typically t#diSi is from about 4 to about 450, preferably at least about 15 to about 350, more preferably from about 30 to about 250, even more preferably from about 60 to about 250; typically % Si is from about 5 to about 90, preferably from about 8 to about 80, more preferably from about 10 to about 70, and even more preferably from about 12 to about 60; for ease of formulation in aqueous compositions, % Si is preferably equal or less than about 50%; and typically t#EO is from about 25 to about 2,000, preferably from about 40 to about 1,500, more preferably from about 60 to about 1,200, and even more preferably from about 100 to about 1,000. Preferably % EO, the weight percent of all of the ethyleneoxy $CH_2CH_2O$ units in the molecule, is less than about 80, preferably from about 10 to about 75, more preferably from about 15 to about 70, and even more preferably from about 25 to about 50; and EO/tail, the average number of ethyleneoxy $CH_2CH_2O$ units per pendant group, is typically less than about 100, preferably less than about 75, more preferably less than about 50, and even more preferably less than about 40.

(B) optionally, an effective amount of fabric wrinkle control agent, preferably selected from the group consisting of fabric lubricant, shape retention polymer, fabric care polysaccharide, hydrophilic plasticizer, and mixtures thereof, preferably from about 0.05% to about 5%, more preferably from about 0.2% to about 3%, even more preferably from about 0.3% to about 2% by weight of the usage composition (with concentrated compositions having a level of from about 1% to about 20%, preferably from about 2% to about 15%, more preferably from about 3% to about 10%, by weight of the composition, of fabric wrinkle control agent);

(C) optionally, but preferably, an effective amount to provide olfactory effects of perfume, preferably from about 0.003% to about 0.5%, more preferably from about 0.01% to about 0.3%, and even more more preferably from about 0.05% to about 0.2%, by weight of the composition of perfume (with concentrated compositions having a level of from about 0.01% to about 5%, preferably from about 0.1% to about 2%, more preferably from about 0.3% to about 1%, by weight of the composition, of perfume), preferably a perfume containing at least about 25%, preferably at least about 40%, more preferably at least about 60%, even more preferably at least about 75%, by weight of the perfume composition of substantive perfume ingredients that have a boiling point of at least about 240° C.; and optionally, a minor amount of perfume ingredients selected from the group consisting of allyl amyl glycolate, ambrox, anethole, bacdanol, benzyl acetone, benzyl salicylate, butyl anthranilate, calone, cetalox, cinnamic alcohol, coumarin, cyclogalbanate, Cyclal C, cymal, damascenone, alpha-damascone, 4-decenal, dihydro isojasmonate, gamma-dodecalactone, ebanol, ethyl anthranilate, ethyl-2-methyl butyrate, ethyl methylphenyl glycidate, ethyl vanillin, eugenol, flor acetate, florhydral, fructone, frutene, heliotropin, herbavert, cis-3-hexenyl salicylate, indole, alpha-ionone, beta-ionone, iso cyclo citral, isoeugenol, alpha-isomethylionone, keone, lilial, linalool, lyral, methyl anthranilate, methyl dihydrojasmonate, methyl heptine carbonate, methyl isobutenyl tetrahydropyran, methyl beta naphthyl ketone, methyl nonyl ketone, beta naphthol methyl ether, nerol, para-anisic aldehyde, para hydroxy phenyl butanone, phenyl acetaldehyde, gamma-undecalactone, undecylenic aldehyde, vanillin, and mixtures thereof;

(D) optionally, an effective amount to clarify the composition and/or improve the performance of the composition, preferably from about 0.05% to about 5%, more preferably from about 0.1% to about 3%, and even more preferably from about 0.2% to about 1.5%, by weight of the usage composition, of surfactant, preferably nonionic surfactant (with concentrated compositions having a level of from about 0.1% to about 15%, preferably from about 0.2% to about 8%, more preferably from about 0.3% to about 5%, by weight of the composition, of surfactant);

(E) optionally, an effective amount, to kill, or reduce the growth of microbes, of antimicrobial active, preferably from about 0.001% to about 0.8%, more preferably from about 0.002% to about 0.3%, even more preferably from about 0.003% to about 0.2%, by weight of the composition, and preferably selected from the group consisting of halogenated compounds, cyclic nitrogen compounds, quaternary compounds, and phenolic compounds (with concentrated compositions having a level of from about 0.003% to about 2%, preferably from about 0.01% to about 1.2%, more preferably from about 0.1% to about 0.8%, by weight of the composition, of antimicrobial active);

(F) optionally, an effective amount to assist in antimicrobial action of aminocarboxylate chelator; preferably from about 0.001% to about 0.3%, preferably from about 0.01% to about 0.1%, more preferably from about 0.02% to about 0.05%, by weight of the usage composition;

(G) optionally, an effective amount to control malodor, typically present at a level of from about 0.01% to about 5%, preferably from about 0.1% to about 4%, more preferably from about 0.2% to about 3%, and even more preferably from about 0.3% to about 2%, by weight of the composition (with concentrated compositions which are meant to be diluted, containing from about 1% to about 20%, preferably from about 1% to about 10%, more preferably from about 2% to about 5%, by weight of the composition), of odor controlling agent, preferably selected from the group consisting of uncomplexed cyclodextrins; zinc and copper salts; soluble carbonate and/or bicarbonate salts; water soluble ionic polymers; and mixtures thereof; more preferably uncomplexed cyclodextrin; water soluble zinc salts; water soluble anionic polymers, and mixtures thereof;

(H) optionally, an effective amount of antimicrobial preservative, preferably from about 0.0001% to about 0.5%, more preferably from about 0.0002% to about 0.2%, most preferably from about 0.0003% to about 0.1%, by weight of the composition;

(I) optionally, an effective amount of adjunct quaternary ammonium fabric softening agent to provide additional fabric softening benefit, typically present at a level of from about 0.05% to about 3%, preferably from about 0.1% to about 2%, more preferably from about 0.3% to about 1%, by weight of the usage composition; and (J) aqueous carrier;

said composition preferably containing at least one of (B) through (I), and wherein said methods of using said compositions preferably does not comprise an ironing step.

The present invention also relates to the compositions incorporated into a spray dispenser (sprayer) to create an article of manufacture that can facilitate treatment of fabric articles and/or surfaces with said compositions containing polyethyleneoxy polysiloxane and other optional ingredients at a level that is effective, yet is not discernible when dried on the surfaces. The spray dispenser comprises both manually activated and non-manual operated spray means and a container containing the fabric softening composition. The articles of manufacture preferably are packaged in association with instructions for use to direct the consumer to use the composition to treat fabrics correctly, including, e.g., the manner and/or amount of composition to spray, e.g., to apply an effective amount of the fabric softening composition and/orpolyethyleneoxy polysiloxane to the fabric,to provide the desired benefit. As used herein, the phrase "in association with" means the instructions are either directly printed on the container itself or presented in a different manner including, but not limited to, a brochure, print advertisement, electronic advertisement, and/or verbal communication, so as to communicate the set of instructions to a consumer of the article of manufacture. It is important that the instructions be as simple and clear, so that using pictures and/or icons may be desirable.

Preferably, the fabric softening composition of the present invention is clear. The term "clear" as defined herein means transparent or translucent, preferably transparent, as in "water clear," when observed through a layer having a thickness of less than about 10 cm.

The present invention also relates to concentrated compositions, wherein the level of of polyethyleneoxy polysiloxane is from about 1% to about 40%, preferably from about 2% to about 20%, more preferably from about 3% to about 10%, by weight of the composition. The concentrated composition is typically diluted to form compositions with the usage concentrations of polyethyleneoxy polysiloxane of, e.g., from about 0.1% to about 5%, by weight of the diluted composition, as given hereinabove, which are the "usage conditions". Specific levels of other optional ingredients in the concentrated composition can readily be determined from the desired usage composition and the desired degree of concentration. These concentrated compositions can be used in a process for preparing large volumes of treatment composition in which water is added, either in a separate container, or in the container of the article of manufacture comprising the spray means.

Alternatively, a relatively concentrated composition can be applied directly on wet fabrics, e.g., fabrics that have been just washed and not yet dried, so that the polyethyleneoxy polysiloxane can be diluted in situ on the wet fabrics. Compositions for use to apply on wet fabrics typically comprises polyethyleneoxy polysiloxane at a level of from about 0.1% to about 20%, preferably from about 0.2% to about 5%, and more preferably from about 0.3% to about 3%, by weight of the composition.

Also preferred are fabric softening compositions for treating fabric in the drying step, comprising an effective amount of polyethyleneoxy polysiloxane, and optionally, adjunct ingredients, e.g., fabric wrinkle control agent, perfume, odor controlling agent, and mixtures thereof. The dryer-added fabric care composition is preferably provided as part of an article of manufacture in combination with a dispensing means such as a flexible substrate or a sprayer which effectively releases the fabric care composition in an automatic tumble clothes dryer.

The fabric softening composition of the present invention can optionally provide one of other fabric care benefits: wrinkle removal, wrinkle reduction, fabric color restoration, and/or static control. The fabric softening composition of the present invention can also contain optional ingredients to additionally provide at least one of the following fabric care benefits: wrinkle removal, wrinkle reduction, wrinkle resistance, fabric wear reduction, fabric wear resistance, fabric pilling reduction, fabric color maintenance, fabric color fading reduction, fabric color restoration, fabric soiling reduction, fabric soil release, fabric shape retention, and/or fabric shrinkage reduction, in a package in association with instructions for use which direct the consumer to apply at least an effective amount of said composition to provide at least one of said fabric care benefits. Many optional ingredients are given hereinabove and/or of the types disclosed in U.S. Pat. Nos. 5,968,404; 5,997,759; and 6,001,343; issued Oct. 19, 1999; Dec. 7, 1999; and Dec. 14, 1999, respectively, to Trinh et al., and U.S. Pat. No. 6,033,679 issued Mar. 7, 2000 to Woo et al., all of said patents are incorporated herein by reference.

The present invention also relates to a method of using Correlation I to (a) estimate and/or predict the fabric softening performance of a polyalkyleneoxy silicone, (b) select or identify the preferred polyalkyleneoxy silicones, and/or (c) design preferred polyalkyleneoxy silicones that provide superior fabric softening performance in fabric care compositions in general, and especially for use in the fabric softening composition of the present invention, as well as fabric care methods and/or articles of manufacture that use such fabric care compositions. Thus the present invention relates to a method using Correlation I hereinabove to design novel polyalkyleneoxy polysiloxanes to provide superior fabric softening benefit via aqueous compositions for direct application, by setting the S value at 15 or higher, preferably at 20 or higher, more preferably at 25 or higher, and even more preferably at 30 or higher; and wherein t#diSi is set at from about 4 to about 450, preferably from about 15 to about 350, more preferably from about 30 to about 250, and even more preferably from about 60 to about 250;

wherein % Si is set from about 5 to about 90, preferably from about 8 to about 80, more preferably from about 10 to about 70, and even more preferably from about 12 to about 60;

wherein t#EO is set from about 25 to about 2,000, preferably from about 40 to about 1,500, more preferably from about 60 to about 1,200, and even more preferably from about 100 to about 1,000;

and wherein the molecular weight of at least about 1,200, preferably from about 2,000 to about 200,000, more preferably from about 4,000 to about 150,000, even more preferably from about 5,000 to about 120,000, and yet more preferably from about 6,000 to about 100,000.

The present invention further includes the novel polyalkyleneoxy polysiloxanes that are derived from the method disclosed above using Correlation I, comprising the polyalkyleneoxy polysiloxanes that do not currently exist and/or commercially available. The present invention also relates to the use of said novel polyalkyleneoxy polysiloxanes to provide fabric softening benefit using aqueous compositions. The present invention further relates to the use of said polyalkyleneoxy polysiloxanes to provide one of other fabric care benefits: wrinkle removal, wrinkle reduction, fabric color restoration, fabric color rejuvenation and/or static control.

All of the patents, patent applications, and references referred to herein are incorporated, either wholly, or in relevant part, by reference. All parts, ratios, and percentages herein are by weight and all numerical limits are used with the normal degree of accuracy afforded by the art unless otherwise specified.

I. Composition (A) Polyalkyleneoxy Polysiloxanes

Polyalkyleneoxy polysiloxanes are also known by other names, including silicone copolyols, silicone glycol copolymers, silicone glycol surfactants, silicone polyoxyalkylene copolymers, silicone poly(oxyalkylene) copolymers, siloxane polyethers, polyalkylene oxide polysiloxanes, polyalkylene oxide silicone copolymers, and dimethicone copolyols. Polyalkyleneoxy polysiloxanes useful as fabric softening active in the composition of the present invention comprise a polysiloxane polymer backbone and one or more polyalkyleneoxy side chains, and having the general formula:

$$R^1\text{—}(CH_3)_2SiO\text{—}[(CH_3)_2SiO]_a\text{—}[(CH_3)(R^1)SiO]_b\text{—}Si(CH_3)_2\text{—}R^1$$

wherein each $R^1$ is the same or different and is selected from the group consisting of $C_1$-$C_4$ alkyl group, preferably methyl; phenyl; polyethyleneoxy/polypropyleneoxy group; optionally $C_2$ to $C_8$ alkenyl group, especially an allyl group; and mixtures thereof; with at least one $R^1$ being a polyethyleneoxy/polypropyleneoxy group, wherein the polyethyleneoxy/polypropyleneoxy group has the general formula:

$$\text{—}(CH_2)_nO(C_2H_4O)_c(C_3H_6O)_dR^2$$

wherein n is 3 or 4, and each $R^2$ is the same or different and is selected from the group consisting of hydrogen, $C_1$-$C_4$ alkyl group, and/or acetyl group, preferably hydrogen and/or methyl group;

said polyalkyleneoxy polysiloxane is selected from the group consisting of polyethyleneoxy polysiloxanes (c is not 0 and d=0), polyethyleneoxy/polypropyleneoxy polysiloxanes (both c and d are not 0), and mixtures thereof;

said polyalkyleneoxy polysiloxane has a molecular weight of at least about 1,200, preferably from about 2,000 to about 200,000, more preferably from about 4,000 to about 150,000, even more preferably from about 5,000 to about 120,000, and yet more preferably from about 6,000 to about 100,000; and said polyalkyleneoxy polysiloxane is characterized by Correlation I:

$$S=3.246(\sqrt{t\#diSi})-1.880(\sqrt{\%Si})-0.9066\sqrt{t\#EO}+17.70 \quad (I)$$

wherein t#diSi is the average total number of the $Si(CH_3)_2O$ units in the molecule; % Si is the weight percent of total silicone (or siloxane) in the molecule; t#EO is the average total number of the ethyleneoxy $CH_2CH_2O$ units in the molecule; and S is the Softness Index which is typically at least about 10, preferably at least about 15, more preferably at least about 20, even more preferably at least about 25, yet more preferably at least about 30; typically t#diSi is from about 4 to about 450, preferably at least about 15 to about 350, more preferably from about 30 to about 250, even more preferably from about 60 to about 250; typically % Si is from about 5 to about 90, preferably from about 8 to about 80, more preferably from about 10 to about 70, and even more preferably from about 12 to about 60; for ease of formulation in aqueous compositions, % Si is preferably equal or less than about 50%; and typically t#EO is from about 25 to about 2,000, preferably from about 40 to about 1,500, more preferably from about 60 to about 1,200, and even more preferably from about 100 to about 1,000. Typical % EO, the weight percent of all of the ethyleneoxy $CH_2CH_2O$ units in the molecule, is less than about 80, preferably from about 10 to about 75, more preferably from about 15 to about 70, and even more preferably from about 25 to about 50; and EO/tail, the average number of ethyleneoxy $CH_2CH_2O$ units per pendant group, is typically less than about 100, preferably less than about 75, more preferably less than about 50, and even more preferably less than about 40.

Correlation I is identified using an quantitative structure-activity relationship (QSAR) method as is described in Applicants' copending U.S. Ser. No., entitled "Predictive Method For Polymers", U.S. Ser. No. 09/989,602 filed Nov. 20, 2001 (now U.S. Pat. No. 6,687,621, granted Feb. 03, 2004), in the name of Schneiderman, et al., said application being incorporated herein by reference.

The most common molecular structures for polyalkyleneoxy polysiloxanes include the graft copolymers (also called the rake-type or comb copolymers, or the alkyl-pendant copolymers) and the ABA copolymers. The graft copolymers have the general structure:

$$(CH_3)_3SiO\text{—}[(CH_3)_2SiO]_a\text{—}[(CH_3)(R^1)SiO]_b\text{—}Si(CH_3)_3$$

wherein the polyalkyleneoxy groups ($R^1$) are attached along a linear polysiloxane backbone through a series of hydrolytically stable Si—C bonds. A special type of graft copolymers are the "trisiloxanes" wherein a=0 and b=1.

The ABA copolymers are linear and have the general structure:

$$R^1\text{—}(CH_3)_2SiO\text{—}[(CH_3)_2SiO]_a\text{—}Si(CH_3)_2\text{—}R^1.$$

Methods for Structural Characterization and Generation of Structural Descriptors for Polyalkyleneoxy Polysiloxanes $^{29}$Si—NMR and $^{13}$C—NMR methods, and hydroiodic acid sample hydrolysis followed by the quantitative GC analysis of the resulting alkyliodides are used to structurally characterize polyalkyleneoxy polysiloxanes of the graft type and the ABA type.

The $^{29}$Si—NMR spectra are obtained at 59.70 MHz using a Fourier transform spectrometer. Chromium (1,3-pentanedione)$_3$ is added to speed up the relaxation and suppress the nuclear Overhauser effect, caused by proton decoupling, on the silicon spectra. The $^{29}$Si—NMR spectra can differentiate and help to quantitatively yield the average number of Si atoms of different siloxane units, viz., the trimethylsiloxane $(CH_3)_3SiO$ units, the dimethylsiloxane $Si(CH_3)_2$—O units, and/or the methyl(alkylene)siloxane $Si(CH_3)(C_nH_{2n})O$ units that link with the poly(alkyleneoxy) groups wherein n is typically 3.

The $^{13}$C—NMR spectra are obtained at 75.57 MHz using a Fourier transform spectrometer. The chromium (1,3-pentanedione)$_3$ added to aid acquiring the silicon spectra, does not cause excessive broadening of the $^{13}$C spectra. The $^{13}$C—NMR spectra yield structural information of all of the carbon groups and are used to determine the average number of pendant groups, the type of pendant groups, the capping groups, and the average number of unreacted allyl groups, if present.

Polyalkyleneoxy polysiloxanes are hydrolyzed by hydroiodic acid, a reaction catalyzed by adipic acid, to produce iodoethane, 1-iodopropane and 2-iodopropane. The hydrolyzed samples (hydrolysates) comprising iodoethane, 1-iodopropane and 2-iodopropane, are analyzed by gas chromatography with the FID detection against an internal standard (octane) and an external standard calibration with iodoalkanes to obtain the mass ratio of the ethyleneoxy units (designated as $w_{EO}$) and the mass ratio of the propyleneoxy units (designated as $w_{PO}$) in the polyalkyleneoxy polysiloxane molecules. The sum of mass ratio of all siloxane units (designated as $w_{Si}$), ethyleneoxy units and propyleneoxy units is equal to 1:

$$w_{Si}+w_{EO}+w_{PO}=1$$

The partial molecular weight of all siloxane units is determined from the average number of individual siloxane units determined from $^{29}Si$— and $^{13}C$—NMR and the respective molecular weight of the individual units according to the equation:

$$MW\text{of all siloxane units}=2*89+(t\#diSi)*74+\#linking\ units*101$$

wherein 74 is the molecular weight of each dimethylsiloxane unit, 89 is the molecular weight of each trimethylsiloxane unit, and 101 is the molecular weight of each linking siloxane $SiMe(CH_2CH_2CH_2)O$ unit. When the linking groups are different from $CH_2CH_2CH_2$, or when the molecule has only one or no $SiMe_3O$ unit, the calculation can be modified accordingly.

Molecular weight of each polyalkyleneoxy polysiloxane molecule, designated as MW, is estimated from the mass ratio of all siloxane units, $w_{Si}$, (with $w_{Si}=1-w_{EO}-w_{PO}$) and the corresponding partial molecular weight of all siloxane units by the following equation:

$$MW=MW\text{of all siloxane units}/w_{Si}$$

The average total number of ethyleneoxy units, —$CH_2CH_2O$—, designated as t#EO, and the average total number of propyleneoxy units, —$CH(CH_3)CH_2O$—, designated as t#PO, are derived from the molecular weight MW of the polyalkyleneoxy polysiloxane, the mass ratio $w_{EO}$ of the ethyleneoxy units and the mass ratio $w_{PO}$ of the propyleneoxy units, respectively, by the following equations:

$$t\#EO=MW*w_{EO}/44 \text{ and}$$

$$t\#PO=MW*w_{PO}/58$$

wherein 44 is the molecular weight of one ethyleneoxy unit —$CH_2CH_2O$—, and 58 is the molecular weight of one propyleneoxy unit —$CH(CH_3)CH_2O$—.

Weight % of all EO units (% EO), weight % of all PO units (% PO), and weight % of all siloxane units (% Si), are obtained by the following equations:

$$\%EO=100\ w_{EO}=100*t\#EO*44/MW$$

$$\%PO=100w_{PO}=100*t\#EO*58/MW, \text{ and}$$

$$\%Si=100w_{Si}=100-\%EO-\%PO$$

The average number of ethyleneoxy units and the average number of propyleneoxy units, respectively, per polyalkyleneoxy group are calculated by dividing the average total number of these units by the sum of the average number of methyl(alkylene)siloxane $Si(CH_3)(C_nH_{2n})O$ units and the average number of unreacted allyl groups according to the following equation:

$$\#EO/\text{group}=t\#EO/(\#Si(CH_3)(C_nH_{2n})O+\text{average \# of unreacted allyl groups})$$

$$\#PO/\text{group}=t\#PO/(\#Si(CH_3)(C_nH_{2n})O+\text{average \# of unreacted allyl groups})$$

The weight % of silicon, designated as % Si atom, is calculated by the ratio of the total number of all siloxane groups multiplied by the molecular weight of silicon and divided by the MW:

$$\%Si\ atom=100*\text{total \# of all siloxane groups}*28/MW$$

For the structural description of the polyalkyleneoxy polysiloxanes, several linear transforms of the structural parameters, such as log(t#Si), $\sqrt{(t\#Si)}$, 1/t#Si, $\sqrt{(t\#diSi)}$, $\sqrt{(\%\ Si)}$, log(t#EO), log(t#PO), $\sqrt{(t\#EO)}$, $\sqrt{(t\#PO)}$, $\sqrt{(\#EO/tail)}$, $\sqrt{(\#PO/tail)}$ have also been found useful.

Preferred polyalkyleneoxy polysiloxanes of the present invention are water soluble or water dispersible. This property is controlled by the average number of ethyleneoxy units in the polyether chain ($R^1$), with higher content (percent by weight in the composition) of ethyleneoxy units corresponds to higher water solubility. Polyalkyleneoxy polysiloxanes which are water insoluble or not readily dispersible in water can be incorporated into the compositions of the present invention by using a suitable emulsifier, preferably nonionic surfactant. Polyalkyleneoxy polysiloxanes comprising only propyleneoxy units, and without ethyleneoxy units are not preferred to use alone, but can be used in mixtures with other emulsifiers and/or suitable polyalkyleneoxy polysiloxanes, preferably polyethyleneoxy polysiloxanes which can serve as emulsifiers in the composition.

Typical levels of polyalkyleneoxy polysiloxane in usage compositions for usage conditions are from about 0.01% to about 10%, preferably from about 0.1% to about 5%, more preferably from about 0.2% to about 3%, and even more preferably from about 0.3% to about 2%, by weight of the usage composition. Typical levels of polyalkyleneoxy polysiloxane in concentrated compositions, to be diluted with water to form compositions with the usage concentrations, are from about 1% to about 40%, preferably from about 2% to about 20%, more preferably from about 3% to about 10%, by weight of the concentrated compositions.

Nonlimiting examples of polyalkyleneoxy polysiloxanes suitable for use in the compositions of the present invention are, e.g., the Silwet® surfactants which are available from OSi Specialties, Inc., Danbury, Conn.; DC silicone copolyols which are available from Dow Corning Corporation, Midland, Mich.; GE Silicones, Waterford, N.Y.; and Goldschmidt Chemical Corp., Hopewell, Va. Nonlimiting examples of suitable polyalkyleneoxy polysiloxanes that are commercially available, are as follows:

| Name | t#diSi[a] | t#EO[b] | % Si[c] | S Value[d] |
|---|---|---|---|---|
| DC-2 5573 | 194 | 754 | 19 | 30 |
| DC-190 | 116 | 411 | 20 | 26 |
| Silwet L-7230 | 68 | 151 | 24 | 24 |
| Silwet L-7001 | 82 | 254 | 20 | 24 |
| Silwet L-7622 | 90 | 107 | 62 | 24 |
| Sliwet L-7087 | 75 | 263 | 18 | 23 |
| DC Q2 5220 | 137 | 854 | 15 | 22 |
| Silwet L-7220 | 40 | 91 | 17 | 22 |
| Silwet L-7200 | 62 | 333 | 21 | 18 |
| Silwet L-7210 | 17 | 71 | 12 | 17 |
| Silwet L-7002 | 25 | 127 | 17 | 16 |
| Silwet L-7602 | 24 | 42 | 56 | 14 |
| Silwet L-7644 | 21 | 54 | 48 | 13 |
| Silwet L-7604 | 20 | 61 | 48 | 12 |
| Silwet L-7657 | 18 | 66.4 | 45 | 11 |
| Silwet L-8620 | 13 | 20 | 57 | 11 |
| Silwet L-8600 | 8 | 25 | 42 | 10 |

[a]Approximated total average number of the $Si(CH_3)_2O$ units in the molecule.
[b]Approximated total average number of the ethyleneoxy $CH_2CH_2O$ units in the molecule.
[c]Approximated percent siloxane in the molecule.
[d]Softness Index as derived from Correlation I.

Comparative Polyethyleneoxy Polysiloxanes: The following comparative polyalkyleneoxy polysiloxanes represent silicones that have an S value of less than about 10, and thus are not suitable for use as fabric softener actives of the present invention.

| Name | t#diSi | t#EO | % Si | S Value |
|---|---|---|---|---|
| DC 2 5237 | 11 | 233 | 10 | 9 |
| Silwet L-7600 | 6.5 | 70 | 32 | 8 |
| Silwet L-7280 | 0 | 9 | 29 | 5 |
| Silwet L-77 | 0 | 10 | 37 | 3 |
| Silwet L-7607 | 0 | 17 | 32 | 3 |
| Silwet L-7608 | 0 | 8 | 44 | 3 |

Trisiloxane polymers such as Silwet® L-77 and L-7608 are not suitable for use as fabric softener actives in the compositions of the present invention, but they can be useful to help distribute and spread the composition on certain fabrics, so they are preferred for their wetting property. When Silwet® L-77 and/or L-7608 are present, the pH of the compositions is preferred to be maintained from about 6.0 to about 8.0, preferably from about 6.5 to about 7.5, and more preferably from about 6.7 to about 7.3.

The present invention also relates to a method of using Correlation I to (a) estimate and/or predict the fabric softening performance of a polyalkyleneoxy polysiloxane, (b) select or identify the preferred polyalkyleneoxy polysiloxanes, and/or (c) design preferred polyalkyleneoxy polysiloxanes that provide superior fabric softening performance in fabric care compositions in general, and especially for use in the fabric softening composition of the present invention, as well as fabric care methods and/or articles of manufacture that use such fabric care compositions.

Procedure to Estimate and/or Predict Fabric Softening Performance of a polyalkyleneoxy polysiloxane: This is done by first determining the structural parameters required by Correlation I, and then calculate the S value using Correlation I:

(a) Determine the approximated average total number of the $SiMe_2O$ units in the molecule (t#diSi), the number of methyl(alkylene)siloxane $Si(CH_3)(C_nH_{2n})O$ units, and total average number of siloxane units t#Si by $^{29}Si$—NMR and $^{13}C$—NMR methods as described hereinabove.

(b) Determine the approximated weight ratio of ethyleneoxy units $w_{EO}$, propyleneoxy units $w_{PO}$, and silicone units $w_{Si}$, per one polymer molecule, by the GC method as described hereinabove.

$$w_{Si}=1-w_{EO}-w_{PO}$$

(c) Determine the approximated average molecular weight (MW) of the polyalkyleneoxy polysiloxane by a combination of $^{29}Si$—NMR method and GC analysis of the hydrolysate of the polyalkyleneoxy polysiloxane as described hereinabove.

(d) Determine the approximated average total number of ethyleneoxy EO units (t#EO), and the approximated average total number of propyleneoxy PO units (t#PO) by the GC method as described hereinabove. The approximated weight percent total EO (% EO) and the weight percent total PO (% PO) are derived from t#EO and t#PO by the equations:

$$\% EO=100*w_{EO}=100\times(t\#EO\times44)/MW$$

$$\% PO=100*w_{PO}=100\times(t\#PO\times58)/MW$$

(e) Determine the approximated weight percent of all siloxane units (% Si) from the mass balance equation $$\% Si=100*w_{Si}=100-\% EO-\% PO$$

(f) Calculate the estimated/predicted softness index S value from mathematical function I by using the above values for t#diSi, t#EO, and % Si. Procedure to Design Preferred Novel Polyalkyleneoxy Polysiloxanes: Correlation I provides a method for designing novel polyalkyleneoxy polysiloxanes that have not been prepared before that can provide superior fabric softening performance in the fabric softening compositions of the present invention. The method allows some flexible choices in designing new molecules, including, but not limited to, (i) choice of preferred type of molecules, e.g., polyethyleneoxy polysiloxane or polyethyleneoxy/polypropyleneoxy polysiloxane; (ii) choice of preferred molecular weight range; and/or (iii) choice of degree of hydrophicity/water compatibility by setting the preferred weight % of all ethyleneoxy EO units and the weight % of all siloxane units. A typical procedure includes the following steps to design a polyalkyleneoxy polysiloxane (wherein the polyalkyleneoxy groups are linked to the silicone backbone by the $CH_2CH_2CH_2$ linking groups, with no unreacted allyl groups, and the molecule has two terminal $SiMe_3O$ siloxane units):

(a) Set a desired S value, typically at least about 15, preferably at least about 25, more preferably at least about 30, still more preferably at least about 32 and yet more preferably at least about 34.

(b) Set a desired average molecular weight, MW, typically at least from about 1,200, preferably from about 2,000 to about 200,000, more preferably from about 4,000 to about 150,000, even more preferably from about 5,000 to about 120,000, and yet more preferably from about 6,000 to about 100,000.

(c) Set a desired weight % of all ethyleneoxy EO units (% EO) for the molecule, typically less than about 80, preferably from about 10 to about 75, more preferably from about 15 to about 70, and even more preferably from about 25 to about 50. The average total number of the ethyleneoxy units in the molecule (t#EO) is then derived from the equation $$\%EO=100\times(t\#EO\times44)/MW$$

wherein t#EO is typically from about 25 to about 2,000, preferably from about 40 to about 1,500, more preferably from about 60 to about 1,200, and even more preferably from about 100 to about 1,000.

(d) Choose the type of polyalkyleneoxy polysiloxane, viz., polyethyleneoxy polysiloxane or polyethyleneoxy/polypropyleneoxy polysiloxane, then set the desired % Si, that is the weight % of all siloxane units (which include the terminal trimethylsiloxane $Me_3SiO$ units, the dimethylsiloxane $SiMe_2O$ units, and/or the linking siloxane SiMe $(CH_2CH_2CH_2)O$ units that link to the polyalkyleneoxy groups). For polyethyleneoxy polysiloxane % EO+% Si=100, while for polyethyleneoxy/polypropyleneoxy polysiloxane % EO+% PO+% Si=100.

(e) Use the desired values for S, t#EO and % Si to calculate t#diSi (the approximated average total number of dimethylsiloxane $SiMe_2O$ units in the molecule), using Correlation I, wherein t#diSi is typically from about 4 to about 450, preferably at least about 15 to about 350, more preferably from about 30 to about 250, even more preferably from about 60 to about 250;

(e) Calculate the average total number of all siloxane groups according to the following Equation $$t\#Si=1.119*t\#diSi+3.788$$

(g) The average number of the polyalkyleneoxy pendant groups are t#linkSi=t#Si−t#diSi−2 for branched graft copolymers.

When the molecule has only one or none SiMe$_3$O unit, the calculation can be modified accordingly.

Nonlimiting examples of the preferred polyethyleneoxy polysiloxanes which are derived from Correlation I and useful in the compositions of the present invention includes:

| Ex. No. | MW | % EO | % PO | % Si | t#diSi | No. of Tails[a] | t#EO | t#PO | Predicted S |
|---|---|---|---|---|---|---|---|---|---|
| 1 | 37,400 | 43 | 6 | 51 | 217 | 28 | 366 | 39 | 35 |
| 2 | 32,100 | 42 | 0 | 58 | 212 | 27 | 306 | 0 | 35 |
| 3 | 40,000 | 42 | 12 | 46 | 212 | 27 | 382 | 83 | 34 |
| 4 | 57,200 | 39 | 27 | 34 | 219 | 28 | 507 | 266 | 34 |
| 5 | 47,400 | 36 | 26 | 38 | 205 | 26 | 388 | 212 | 35 |
| 6 | 33,300 | 34 | 16 | 50 | 190 | 24 | 257 | 92 | 35 |
| 7 | 78,300 | 30 | 46 | 24 | 212 | 27 | 534 | 621 | 35 |
| 8 | 36,200 | 30 | 26 | 44 | 181 | 23 | 247 | 162 | 35 |
| 9 | 27,300 | 28 | 14 | 58 | 180 | 23 | 174 | 66 | 35 |
| 10 | 32,700 | 26 | 29 | 45 | 168 | 22 | 193 | 164 | 35 |
| 11 | 89,800 | 22 | 59 | 19 | 190 | 24 | 449 | 913 | 35 |
| 12 | 63,500 | 10 | 73 | 17 | 121 | 16 | 144 | 799 | 35 |
| 13 | 48,300 | 10 | 69 | 21 | 116 | 16 | 110 | 575 | 35 |
| 14 | 16900 | 16 | 0 | 84 | 161 | 21 | 61 | 0 | 35 |
| 15 | 31500 | 43 | 0 | 57 | 205 | 26 | 306 | 0 | 34 |
| 16 | 21100 | 26 | 0 | 74 | 177 | 23 | 127 | 0 | 35 |
| 17 | 43,000 | 51 | 4 | 45 | 220 | 28 | 498 | 30 | 33 |
| 18 | 58,900 | 46 | 21 | 33 | 220 | 28 | 616 | 213 | 33 |
| 19 | 51,500 | 40 | 26 | 34 | 202 | 26 | 468 | 231 | 33 |
| 20 | 41,700 | 33 | 32 | 35 | 168 | 22 | 313 | 230 | 33 |
| 21 | 62,500 | 33 | 41 | 26 | 184 | 24 | 469 | 442 | 33 |
| 22 | 23,100 | 31 | 6 | 63 | 166 | 22 | 163 | 24 | 33 |
| 23 | 32,300 | 25 | 34 | 41 | 151 | 20 | 184 | 189 | 33 |
| 24 | 22,900 | 23 | 19 | 58 | 150 | 20 | 120 | 75 | 33 |
| 25 | 23,900 | 22 | 23 | 55 | 147 | 19 | 120 | 95 | 33 |
| 26 | 87,600 | 21 | 63 | 16 | 158 | 21 | 418 | 952 | 32 |
| 27 | 69,900 | 19 | 63 | 18 | 141 | 19 | 302 | 759 | 33 |
| 28 | 33300 | 47 | 0 | 53 | 203 | 26 | 352 | 0 | 33 |
| 29 | 19900 | 28 | 0 | 72 | 162 | 21 | 128 | 0 | 33 |
| 30 | 26300 | 39 | 0 | 61 | 182 | 23 | 234 | 0 | 33 |
| 31 | 49,100 | 59 | 4 | 37 | 206 | 26 | 658 | 34 | 30 |
| 32 | 50,000 | 54 | 11 | 35 | 197 | 25 | 614 | 95 | 30 |
| 33 | 66,400 | 54 | 17 | 29 | 219 | 28 | 815 | 195 | 30 |
| 34 | 30,400 | 48 | 4 | 48 | 165 | 21 | 332 | 21 | 30 |
| 35 | 26,300 | 42 | 5 | 53 | 166 | 21 | 251 | 23 | 31 |
| 36 | 21,400 | 40 | 0 | 60 | 146 | 19 | 195 | 0 | 30 |
| 37 | 32,200 | 40 | 19 | 41 | 150 | 20 | 293 | 105 | 30 |
| 38 | 25,000 | 32 | 23 | 45 | 128 | 17 | 182 | 99 | 30 |
| 39 | 22,700 | 31 | 19 | 50 | 127 | 17 | 160 | 74 | 30 |
| 40 | 34,100 | 28 | 38 | 34 | 132 | 17 | 217 | 223 | 31 |
| 41 | 19,600 | 19 | 34 | 47 | 104 | 14 | 85 | 115 | 30 |
| 42 | 16,100 | 15 | 29 | 56 | 101 | 14 | 55 | 81 | 30 |
| 43 | 41,000 | 12 | 70 | 18 | 82 | 11 | 112 | 495 | 29 |
| 44 | 15300 | 23 | 0 | 77 | 132 | 17 | 81 | 0 | 30 |
| 45 | 26200 | 44 | 0 | 56 | 170 | 22 | 261 | 0 | 31 |
| 46 | 43700 | 58 | 0 | 42 | 208 | 27 | 577 | 0 | 31 |
| 47 | 33,400 | 63 | 0 | 37 | 140 | 18 | 478 | 0 | 25 |
| 48 | 55,900 | 63 | 11 | 26 | 168 | 22 | 800 | 106 | 25 |
| 49 | 39,200 | 62 | 6 | 32 | 144 | 19 | 552 | 41 | 25 |
| 50 | 50,400 | 60 | 12 | 28 | 160 | 21 | 687 | 104 | 25 |
| 51 | 29,100 | 49 | 15 | 36 | 118 | 16 | 324 | 75 | 25 |
| 52 | 23,400 | 46 | 14 | 40 | 104 | 14 | 245 | 56 | 25 |
| 53 | 16,400 | 36 | 16 | 48 | 88 | 12 | 134 | 45 | 25 |
| 54 | 12,900 | 34 | 0 | 66 | 94 | 13 | 100 | 0 | 25 |
| 55 | 22,000 | 32 | 35 | 33 | 81 | 11 | 160 | 133 | 25 |
| 56 | 25,800 | 20 | 57 | 23 | 64 | 9 | 117 | 254 | 25 |
| 57 | 17,800 | 19 | 49 | 32 | 62 | 9 | 77 | 150 | 25 |
| 58 | 15,300 | 16 | 48 | 36 | 60 | 9 | 56 | 127 | 25 |
| 59 | 8700 | 15 | 0 | 85 | 82 | 12 | 29 | 0 | 25 |
| 60 | 12300 | 33 | 0 | 67 | 91 | 13 | 93 | 0 | 25 |
| 61 | 20400 | 52 | 0 | 48 | 110 | 15 | 239 | 0 | 25 |

[a] The average number of tails is t#linkSi, i.e., the average number of polyalkyleneoxy polysiloxane groups in the molecule.

Besides fabric softening, polyalkyleneoxy polysiloxanes can also provide other benefits, such as color restoration, wrinkle reduction, and lubricity to fabrics.

The preparation of polyalkyleneoxy polysiloxanes is well known in the art. Polyalkyleneoxy polysiloxanes of the present invention can be prepared according to the procedure set forth in U.S. Pat. No. 3,299,112, incorporated herein by reference. Typically, polyalkyleneoxy polysiloxanes of the present invention are readily prepared by an addition reaction between a hydrosiloxane (i.e., a siloxane containing silicon-bonded hydrogen) and an alkenyl ether (e.g., a vinyl, allyl, or methallyl ether) of an alkoxy or hydroxy end-blocked polyalkyleneoxy). The reaction conditions employed in addition reactions of this type are well known in the art and in general involve heating the reactants (e.g., at a temperature of from about 85° C. to 110° C.) in the presence of a platinum catalyst (e.g., chloroplatinic acid) and a solvent (e.g., toluene). Additional disclosures of preparation methods for polyalkyleneoxy polysiloxanes can be found in *Silicone Surfactants*, R. M. Hill (Ed.), Marcel Dekker, Inc. (1999), Chapter 2, said publication being incorporated herein by reference.

Although some polyalkyleneoxy polysiloxanes have been prepared and commercially available, and may even have been disclosed generically with a fabric softening benefit, there has been no appreciation that specific polyalkyleneoxy polysiloxanes within the defined parameters herein have highly desirable softening benefit when applied, e.g., as an aqueous spray. The incidental disclosure of the existing polyalkyleneoxy polysiloxanes or commercially available polyalkyleneoxy polysiloxanes does not suggest any reason for preparing other closely related polyalkyleneoxy polysiloxanes. And currently there is no accurate prediction means to guide the preparation of other polyalkyleneoxy polysiloxanes that provide good softness performance in the context os the aqueous spray product. Therefore, the present invention relates to all novel polyalkyleneoxy polysiloxanes capable of providing fabric softening benefit and selected from the group consisting of polyethyleneoxy polysiloxane, polyethyleneoxy/polypropyleneoxy polysiloxanes, and mixtures thereof, having an average molecular weight of from about 3,000 to about 200,000, and being characterized by Correlation I:

$$S=3.246(\sqrt{\#diSi})-1.880(\sqrt{\%Si})-0.9066\sqrt{\#EO}+17.70 \quad (I)$$

wherein the softness index S is at least about 15, preferably at least about 20, and more preferably at least about 25, excluding the incidentally disclosed polyethyleneoxy polysiloxanes, said incidentally disclosed polyethyleneoxy polysiloxanes include: Silwet Silwet L-77, Silwet L-711, Silwet L-720, Silwet L-721, Silwet L-7000, Silwet L-7001, Silwet L-7002, Silwet L-7087, Silwet L-7200, Silwet L-7210, Silwet L-7220, Silwet L-7230, Silwet L-7280, Silwet L-7600, Silwet L-7602, Silwet L-7604, Silwet L-7605, Silwet L-7607, Silwet L-7608, Silwet L-7610, 7614, Silwet L-7622, Silwet L-7644, Silwet L-7650, Silwet L-7657, Silwet L-8500, Silwet L-8600, Silwet L-8610, Silwet L-8620, Silwet FZ-2104, Silwet FZ-2120, Silwet FZ-2161, Silwet FZ-2162, Silwet FZ-2163, Silwet FZ-2164, Silwet FZ-2165, Silwet FZ-2166, Silsoft® 477, Silsoft 487, Silsoft 497, DC 190, DC 193, DC 2 5237, DC-2 5573, DC 3225C, DC 5093, DC 5097, DC 5098, DC 5103, DC 5197, DC 5200, DC 5211, DC 5212, DC 5220, DC 5225C, DC 5237, DC 5247, DC 5329, $DC_{5604}$, DC 8692, DC Q2-2511, DC Q2-5220, DC Q4-3667, FF 400, Sylgard® 309, SH3771C, SH3772C, SH3773C, SH3746, SH3748, SH3749, SH8400, SF8410, SH8700, SF 1188A, SF 1288, SF 1388, SF 1488, SF 1328, SF 1528, TSF 4440, TSF 4441, TSF 4445, TSF 4446, TSF 4452, TSF 4450, OL 17, OL 31, OL 44, AC 3233, AI 3669, AI 3465, AI 3466, AI 3467, AI 3468, VP 3738, VP 3739, TP 3792, TP 3793, TP 3794, TP 3799, TP 3800, TP 3801, TP 3804, TP 3805, TP 3806, Abil® B 8800, Abil B 8830, Abil B 8832, Abil B 8842, Abil B 8843, Abil B 8847, Abil B 8851, Abil B 8852, Abil B 8863, Abil B 8873, Abil EM 97, Abil EM-90, Abil WE-09, Abil B 88183, Abil B 88184, Abil 9950, Abil EM-90, Abil EM-97, Abil WE-90, Abil Care 85, KF351, KF352, KF353, KF354, KF 355, KF615, KF618, KF 625, KF 857, KF 862, KF-888, KF945, KF-8001, X-22-3667, X-22-3939A, X-22-4741, X-22-6008, X-22-8645, Fancorsil® LIM 1, Fancorsil LIM 2, Fancorsil LIM 3, Alkasil® NE 58-50, Alkasil NEP 73-70, Alkasil® NEPCA 250-185, Rhodorsil® Oils 70646, Silbione® Oils 70646, Amersil® DMC-287, Amersil DMC-357, Masil® 1066 D, Masil 280 LP, Silicone Copolymer F-754, Silicone Fluid VP, Belsil® DMC 6031, Belsil DMC 6032, Belsil DMC 6033, Belsil DMC 6035, Troysol® S366, Troysol 380W, and Forbest® G-23. Silwet polyethyleneoxy polysiloxanes are available from CK Witco Corporation, Greenwich, Conn., Silsoft polyethyleneoxy polysiloxanes were available from OSi Specialties, Inc. Danbury, Conn., DC polymers, FF 400, and Sylgard 309 are available from Dow Corning Corporation, Midland, Mich., SH polymers are available from Dow Corning-Toray, SF polymers are available from GE-Silicones, TSF polymers are available from GE-Toshiba, OL, AC, AI, VP, and TP polymers are available from GE-Bayer, Abil polymers are available from Th. Goldschmidt AG, Hopewell, Va., KF and X polymers are available from Shin-Etsu, Fancorsil polymers are available from Fancor, Alkasil, Rhodorsil, and Silbione polymers are available from Rhodia, Inc., Cranbury, N.J., Amersil polymers are available from Amerchol Corp., Edison, N.J., Masil polymers are vailable from PPG/Mazer, Silicone Copolymer F-754, Silicone Fluid VP, and Belsil polymers are available from Wacker, Forbest polymer is available from Lucas Meyer GmbH, Hamburg, Germany, and Troysol polymers are available from Troy Corp., Florham Park, N.J.

(B) Wrinkle Control Agent

The composition can optionally contain an effective amount fabric wrinkle control agent, preferably selected from the group consisting of: fiber lubricants, shape retention polymers, polysaccharides, hydrophilic plasticizers, and mixtures thereof. Effective amount of wrinkle control agent is from about 0.05% to about 5%, preferably from about 0.2% to about 3%, more preferably from about 0.3% to about 2% by weight of the usage composition (with concentrated compositions having a level of from about 1% to about 20%, preferably from about 2% to about 15%, more preferably from about 3% to about 10%, by weight of the concentrated solution).

(1) Fiber Lubricants

The fabric softening composition of the present invention can comprise optional fiber lubricant to impart a lubricating property or increased gliding ability to fibers in fabric, particularly clothing. Preferred fiber lubricants include silicones.

(a) Silicones

The present invention can use silicone to impart a lubricating property or increased gliding ability to fibers in fabric, particularly clothing. Nonlimiting examples of useful silicones include noncurable silicones such as polydimethylsilicone and volatile silicones, and curable silicones such as aminosilicones and hydroxysilicones.

Suitable and preferred silicones that are useful in the compositions of the present invention are disclosed in WO 99/55953 published Nov. 4, 1999 to Trinh et al., said publication is incorporated herein by reference.

When silicone is present, it is present at least an effective amount to provide lubrication of the fibers, typically from about 0.1% to about 5%, preferably from about 0.2% to about 3%, more preferably from about 0.3% to about 2%, by weight of the usage composition.

(b) Synthetic Solid Particles

Solid polymeric particles of average particle size smaller than about 10 microns, preferably smaller than 5 microns, more preferably smaller than about 1 micron, e.g., Velustrol P-40 oxidized polyethylene emulsion available from Clariant, can be used as a lubricant, since they can provide a "roller-bearing" action. When solid polymeric particles are present, they are present at an effective amount to provide lubrication of the fibers, typically from about 0.01% to about 3%, preferably from about 0.05% to about 1%, more preferably from about 0.1% to about 0.5%, by weight of the usage composition.

(2) Shape Retention Polymer

These polymers can be natural, or synthetic, and can act by forming a film, and/or by providing adhesive properties. Suitable and preferred shape retention polymers that are useful in the compositions of the present invention are disclosed in WO 99/55953 published Nov. 4, 1999 to Trinh et al., said publication is incorporated herein by reference.

The optional film-forming and/or adhesive polymer of the present invention is present at least an effective amount to provide shape retention, typically from about 0.05% to about 5%, preferably from about 0.1% to about 3%, more preferably from about 0.2% to about 2%, even more preferably from about 0.3% to about 1%, by weight of the usage composition.

The adhesive polymer is present in the composition in a sufficient amount to result in an amount of from about 0.001% to about 1%, preferably from about 0.01% to about 0.5%, more preferably from about 0.02% to about 0.4% by weight of polymer per weight of dry fabrics.

Concentrated compositions can also be used in order to provide a less expensive product. When a concentrated product is used, i.e., when the wrinkle reducing active is from about 5% to about 50%, by weight of the concentrated composition, it is preferable to dilute the composition before treating fabric. Preferably, the wrinkle reducing active is diluted with about 50% to about 10,000%, more preferably from about 50% to about 8,000%, and even more preferably from about 50% to about 5,000%, by weight of the composition, of water.

Optional silicones and film-forming polymers can be combined to produce preferred wrinkle reducing actives. Typically the weight ratio of silicone to film-forming polymer is from about 10:1 to about 1:10, preferably from about 5:1 to about 1:5, and more preferably from about 2:1 to about 1:2. Typically, the preferred wrinkle reducing active of silicone plus polymer is present at a level of from about 0.1% to about 8%, preferably from about 0.3% to about 5%, more preferably from about 0.5% to about 3%, by weight of the composition.

Optional but preferred adhesive and/or film forming polymers that are useful in the composition of the present invention actually contain silicone moieties in the polymers themselves. These preferred polymers, excluding the silicone copolyols, include graft and block copolymers of silicone with moieties containing hydrophilic and/or hydrophobic monomers. The silicone-containing copolymers in the spray composition of the present invention provide shape retention, body, and/or good, soft fabric feel. The useful copolymers are described in WO 99/55953 published Nov. 4, 1999 to Trinh et al., said publication is incorporated herein by reference.

(3) Fabric Care Polysaccharides

Suitable optional fabric care polysaccharides for use in the composition of the present invention are those which have a globular conformation in dilute aqueous solution, via a random coiling structure. Said polysaccharides include homo- and/or hetero-polysaccharides with simple helical structure with or without branching, e.g., with 1,4-α-linked backbone structure (e.g., 1,4-α-glucan, 1,4-α-xylan) with or without branching, 1,3-β-linked backbone with or without branching (e.g., galactan), and all 1,6-linked backbones with or without branching (e.g., dextran, pullulan, pustulan), and with a weight-average molecular weight of from about 5,000 to about 500,000, preferably from about 8,000 to about 250,000, more preferably from about 10,000 to about 150,000, typically with sizes ranging from about 2 nm to about 300 nm, preferably from about 3 nm to about 100 nm, more preferably from about 4 nm to about 30 nm. The size is defined as the gyration length occupied by the molecule in dilute aqueous solutions. The useful fabric care polysaccharides are described with more details in WO 00/24856 published May 4, 2000 to Barnabas et al., said publication is incorporated herein by reference.

Typical composition to be dispensed from a sprayer contains a level of fabric care polysaccharide with globular structure of from about 0.01% to about 5%, preferably from about 0.05% to about 2%, more preferably from about 0.1% to about 1%, by weight of the usage composition.

(4) Hydrophilic Plasticizer

Optionally, the composition can contain a hydrophilic plasticizer to soften both the fabric fibers, especially cotton fibers, and the adhesive and/or film-forming shape retention polymers. Examples of the preferred hydrophilic plasticizers are low molecular weight polyhydric alcohols, such as is glycerol, ethylene glycol, propylene glycol, diethylene glycol, dipropylene glycol, sorbitol, erythritol, and mixtures thereof, more preferably diethylene glycol, dipropylene glycol, ethylene glycol, propylene glycol and mixtures thereof.

The aqueous compositions containing these plasticizers also tend to provide a slower drying profile for clothing/fabrics, to allow time for any wrinkles to disappear when the clothing/fabrics are hung to dry. This is balanced by the desire by most consumer to have the garments to dry faster. Therefore, when needed, the plasticizers should be used at an effective, but as low as possible, level in the composition. When a hydrophilic plasticizer is used, it is present in the at a level of from 0.01% to 5%, preferably from 0.05% to 2%, more preferably from 0.1% to 1% by weight of the usage composition.

(C) Perfume

The fabric softening composition of the present invention can also optionally provide a "scent signal" in the form of a pleasant odor which provides a freshness impression to the treated fabrics. The scent signal can be designed to provide a fleeting perfume scent. When perfume is added as a scent signal, it is added only at very low levels, e.g., from about 0.001% to about 1%, preferably from about 0.003% to about 0.3%, more preferably from about 0.005% to about 0.2%, by weight of the usage composition.

Perfume can also be added as a more intense odor in product and on fabrics. When stronger levels of perfume are preferred, relatively higher levels of perfume can be added.

Any type of perfume can be incorporated into the composition of the present invention. The preferred perfume ingredients are those suitable for use to apply on fabrics and garments. Typical examples of such preferred ingredients are given in U.S. Pat. No. 5,445,747, issued Aug. 29, 1995 to Kvietok et al., incorporated herein by reference.

As used herein, perfume includes fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders, stabilizers and solvents. These auxiliaries are also included within the meaning of "perfume", as used herein. Typically, perfumes are complex mixtures of a plurality of organic compounds.

Examples of perfume ingredients useful in the perfumes of the present invention compositions include, but are not limited to, those materials disclosed in said patents.

The perfumes useful in the present invention compositions are preferably substantially free of halogenated materials and nitromusks.

Suitable solvents, diluents or carriers for perfumes ingredients mentioned above are for examples, ethanol, isopropanol, diethylene glycol, monoethyl ether, dipropylene glycol, diethyl phthalate, triethyl citrate, etc. The amount of such solvents, diluents or carriers incorporated in the perfumes is preferably kept to the minimum needed to provide a homogeneous perfume solution.

Concentrated fabric softening composition of the present invention can contain higher levels of perfume, up to about 3%, preferably from about 0.01% to about 1%, and more preferably from about 0.1% to about 0.5%, by weight of the finished fabric softening composition.

Preferably, the fabric softening composition herein comprises a perfume comprising substantive perfume ingredients to provide a long lasting perfume odor benefit. It is preferable that at least about 25%, preferably at least about 40%, more preferably at least about 60%, and even more preferably at least about 75%, by weight of the perfume is composed of substantive perfume ingredients; and optionally some perfume ingredients having low odor detection threshold.

Substantive perfume ingredients are characterized by their boiling points (B.P.). The substantive perfume ingredients of this invention have a B.P, measured at the normal, standard pressure of 760 mm Hg, of about 240° C. or higher, and preferably of about 250° C. or higher.

The boiling points of many perfume ingredients are given in, e.g., "Perfume and Flavor Chemicals (Aroma Chemicals)," Steffen Arctander, published by the author, 1969, incorporated herein by reference. Other boiling point values can be obtained from different chemistry handbooks and data bases, such as the Beilstein Handbook, Lange's Handbook of Chemistry, and the CRC Handbook of Chemistry and Physics. When a boiling point is given only at a different pressure, usually lower pressure than the normal pressure of 760 mm Hg, the boiling point at normal pressure can be approximately estimated by using boiling point-pressure nomographs, such as those given in "The Chemist's Companion," A. J. Gordon and R. A. Ford, John Wiley & Sons Publishers, 1972, pp. 30-36. The boiling point values can also be estimated via a computer program that is described in "Development of a Quantitative Structure—Property Relationship Model for Estimating Normal Boiling Points of Small Multifunctional Organic Molecules", David T. Stanton, Journal of Chemical Information and Computer Sciences, Vol. 40, No. 1, 2000, pp. 81-90, incorporated herein by reference. Thus, when a perfume composition is composed of substantive perfume ingredients having a B. P. of about 240° C. or higher, they appreciably remain on fabrics after the drying step.

Non-limiting examples of the preferred substantive perfume ingredients of the present invention include: allyl cyclohexane propionate, ambrettolide, amyl benzoate, amyl cinnamate, amyl cinnamic aldehyde, amyl cinnamic aldehyde dimethyl acetal, iso-amyl salicylate, aurantiol (trade name for hydroxycitronellal-methyl anthranilate), benzophenone, benzyl salicylate, iso-butyl quinoline, beta-caryophyllene, cadinene, cedrol, cedryl acetate, cedryl formate, cinnamyl cinnamate, cyclohexyl salicylate, cyclamen aldehyde, dihydro isojasmonate, diphenyl methane, diphenyl oxide, dodecalactone, iso E super (trade name for 1-(1,2,3,4,5,6,7,8-octahydro-2,3,8,8-tetramethyl-2-naphthalenyl)-ethanone), ethylene brassylate, ethyl methyl phenyl glycidate, ethyl undecylenate, iso-eugenol, exaltolide (trade name for 15-hydroxypentadecanoic acid, lactone), galaxolide (trade name for 1,3,4,6,7,8-hexahydro-4,6,6,7,8,8-hexamethylcyclopenta-gamma-2-benzopyran), geranyl anthranilate, hexadecanolide, hexenyl salicylate, hexyl cinnamic aldehyde, hexyl salicylate, lilial (trade name for para-tertiary-butyl-alpha-methyl hydrocinnamic aldehyde), linalyl benzoate, 2-methoxy naphthalene, methyl cinnamate, methyl dihydrojasmonate, beta-methyl naphthyl ketone, musk indanone, musk ketone, musk tibetine, myristicin, delta-nonalactone, oxahexadecanolide-10, oxahexadecanolide-11, patchouli alcohol, phantolide (trade name for 5-acetyl-1,1,2,3,3,6-hexamethylindan), phenyl ethyl benzoate, phenylethylphenylacetate, phenyl heptanol, phenyl hexanol, alpha-santalol, thibetolide (trade name for 15-hydroxypentadecanoic acid, lactone), tonalid, delta-undecalactone, gamma-undecalactone, vetiveryl acetate, yara-yara, allyl phenoxy acetate, cinnamic alcohol, cinnamic aldehyde, cinnamyl formate, coumarin, dimethyl benzyl carbinyl acetate, ethyl cinnamate, ethyl vanillin (3-methoxy-4-ethoxy benzaldehyde), eugenol, eugenyl acetate, heliotropine, indol, isoeugenol, koavone, methyl-beta-naphthyl ketone, methyl cinnamate, methyl dihdrojasmonate, beta methyl naphthyl ketone, methyl-n-methyl anthranilate, delta-nonalactone, gamma-nonalactone, para methoxy acetophenone (acetanisole), phenoxy ethyl iso butyrate, phenoxy ethyl propionate, piperonal, triethyl citrate, vanillin, and mixtures thereof. Other substantive perfume ingredients useful in the present invention include methyl-N-methyl anthranilate, benzyl butyrate, benzyl iso valerate, citronellyl isobutyrate, citronellyl propionate, delta-nonalactone, dimethyl benzyl carbinyl acetate, dodecanal, geranyl acetate, geranyl isobutyrate, gamma-ionone, para-isopropyl phenylacetaldehyde, cis-jasmone, methyl eugenol, hydroxycitronellal, phenoxy ethanol, benzyl iso valerate, anisic aldehyde, cuminic alcohol, cis-jasmone, methyl eugenol, and mixtures thereof.

The preferred perfume compositions used in the present invention contain at least 4 different substantive perfume ingredients, preferably at least 5 substantive perfume ingredients, more preferably at least 6 different substantive perfume ingredients, and even more preferably at least 7 different substantive perfume ingredients. Most common perfume ingredients which are derived from natural sources are composed of a multitude of components. When each such material is used in the formulation of the preferred perfume compositions of the present invention, it is counted as one single ingredient, for the purpose of defining the invention.

In the perfume art, some materials having no odor or very faint odor are used as diluents or extenders. Non-limiting examples of these materials are dipropylene glycol, diethyl phthalate, triethyl citrate, isopropyl myristate, and benzyl benzoate. These materials are used for, e.g., diluting and stabilizing some other perfume ingredients. These materials are not counted in the formulation of the substantive perfume compositions of the present invention.

Low Odor Detection Threshold Perfume Ingredients

The substantive perfume compositions of the present invention can also comprise some low odor detection threshold perfume ingredients. The odor detection threshold of an odorous material is the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalari, editor, ASTM Data Series DS 48A, American Society for Testing and Materials, 1978, both of said publications being incorporated by reference. The use of small amounts of perfume ingredients that have low odor detection threshold values can improve perfume odor character, even though they are not as materially substantive as the substantive perfume ingredients disclosed hereinabove. Perfume ingredients having a significantly low detection threshold, useful in the substantive perfume composition of the present invention, are selected from the group consisting of allyl amyl glycolate, ambrox, anethole, bacdanol, benzyl acetone, benzyl salicylate, butyl anthranilate, calone, cetalox, cinnamic alcohol, coumarin, cyclogalbanate, Cyclal C, cymal, damascenone, alpha-damascone, 4-decenal, dihydro isojasmonate, gamma-dodecalactone, ebanol, ethyl anthranilate, ethyl-2-methyl butyrate, ethyl methylphenyl glycidate, ethyl vanillin, eugenol, flor acetate, florhydral, fructone, frutene, heliotropin, herbavert, cis-3-hexenyl salicylate, indole, alpha-ionone, beta-ionone, iso cyclo citral, isoeugenol, alpha-isomethylionone, keone, lilial, linalool, lyral, methyl anthranilate, methyl dihydrojasmonate, methyl heptine carbonate, methyl isobutenyl tetrahydropyran, methyl beta naphthyl ketone, methyl nonyl ketone, beta naphthol methyl ether, nerol, para-anisic aldehyde, para hydroxy phenyl butanone, phenyl acetaldehyde, gamma-undecalactone, undecylenic aldehyde, vanillin, and mixtures thereof. These materials are preferably present at low levels in addition to the substantive perfume ingredients, typically less than about 40%, preferably less than about 30%, more preferably less than about 20%, by weight of the total perfume compositions of the present invention. However, only low levels are required to provide a perfume odor effect. Some substantive perfume ingredients also have low odor detection threshold. These materials are counted as substantive perfume ingredients in the formulation of the substantive perfume compositions of the present invention The compositions of the present invention can also comprise a perfume delivery system that can slowly release perfume ingredients after the fabric is treated by the fabric care composition of this invention. Said comprises one or more pro-fragrances, pro-perfumes, pro-accords, and mixtures thereof hereinafter known collectively as "pro-perfumes". The pro-perfumes of the present invention can exhibit varying release rates depending upon the pro-perfume chosen. In addition, the pro-perfumes of the present invention can be admixed with the perfume materials which are released therefrom to present the user with an initial fragrance, scent, accord, or bouquet. Non-limiting examples of pro-perfumes according to the present invention are ester and polyester pro-perfumes, β-ketoester pro-perfumes, acetal and ketal pro-perfumes, orthoester pro-perfumes, and mixtures thereof.

Pro-perfumes are suitably described in the following: U.S. Pat. No. 5,378,468 Suffis et al., issued Jan. 3, 1995; U.S. Pat. No. 5,531,910, Severns et al., issued Jul. 2, 1996, U.S. Pat. No. 5,626,852 Suffis et al., issued May 6, 1997; U.S. Pat. No. 5,710,122 Sivik et al., issued Jan. 20, 1998; U.S. Pat. No. 5,716,918 Sivik et al., issued Feb. 10, 1998; U.S. Pat. No. 5,721,202 Waite et al., issued Feb. 24, 1998; U.S. Pat. No. 5,744,435 Hartman et al., issued Apr. 25, 1998; U.S. Pat. No. 5,756,827 Sivik, issued May 26, 1998; U.S. Pat. No. 5,830,835 Severns et al., issued Nov. 3, 1998; U.S. Pat. No. 5,919,752 Morelli et al., issued Jul. 6, 1999 all of which are incorporated herein by reference.

When cyclodextrin is present for odor control benefit, it is essential that the perfume be added at a level wherein even if all of the perfume in the composition were to complex with the cyclodextrin molecules when cyclodextrin is present, there will still be an effective level of uncomplexed cyclodextrin molecules present in the solution to provide adequate odor control. In order to reserve an effective amount of cyclodextrin molecules for odor control when cyclodextrin is present, perfume is typically present at a level wherein less than about 90% of the cyclodextrin complexes with the perfume, preferably less than about 50% of the cyclodextrin complexes with the perfume, more preferably, less than about 30% of the cyclodextrin complexes with the perfume, and most preferably, less than about 10% of the cyclodextrin complexes with the perfume. The cyclodextrin to perfume weight ratio should be greater than about 8:1, preferably greater than about 10:1, more preferably greater than about 20:1, even more preferably greater than 40:1 and most preferably greater than about 70:1.

Preferably the perfume for use in presence of cyclodextrin is hydrophilic and is composed of hydrophilic perfume ingredients having a ClogP of less than about 3.2, more preferably equal to or less than about 3.0. Said perfume comprises at least about 25% hydrophilic perfume ingredients, preferably at least about 50%, more preferably at least about 75%, by weight of the perfume composition.

Nonlimiting suitable and preferred hydrophilic perfume ingredients and methods to determine ClogP, the calculated logP, are given in U.S. Pat. No. 6,001,343, issued Dec. 14, 1999 to Trinh et al., said patent is incorporated herein by reference.

(D) Surfactant

Surfactant is an optional but preferred ingredient of the present invention. Surfactant is useful in the composition to facilitate the dispersion and/or solubilization of, e.g., polyalkyleneoxy polysiloxanes, wrinkle control agents such as silicones, and/or certain relatively water insoluble adjunct shape retention polymers. Some surfactants, e.g., some nonionic surfactants are especially useful to clarify compositions (make the compositions clear) that comprise polyalkyleneoxy polysiloxanes that are not soluble in water at preferred levels in the compositions. Surfactant is also preferably included when the composition is used in a spray dispenser in order to enhance the spray characteristics of the composition and allow the composition to distribute more evenly, and to prevent clogging of the spray apparatus. The spreading of the composition can also allow it to dry faster, so that the treated material is ready to use sooner. For concentrated compositions, the surfactant facilitates the dispersion of many actives such as antimicrobial actives and perfumes in the concentrated aqueous compositions. Suitable surfactant useful in the present invention is nonionic surfactant, anionic surfactant, cationic surfactant, amphoteric surfactant, and mixtures thereof.

When surfactant is used in the composition of the present invention, it is added at an effective amount to provide one, or more of the benefits described herein, typically from about 0.05% to about 5%, preferably from about 0.1% to about 3%, more preferably from about 0.2% to about 1.5%, and even more preferably, from about 0.2% to about 1%, by weight of the usage composition. Concentrated compositions to be diluted for use comprise higher levels of surfactants, typically from about 0.1% to about 15%, preferably from about 0.2% to about 8%, more preferably from about 0.3% to about 5%, by weight of the concentrated composition.

A preferred type of surfactant is ethoxylated surfactant, such as addition products of ethylene oxide with fatty alcohols, fatty acids, fatty amines, etc. Optionally, addition products of mixtures of ethylene oxide and propylene oxide with fatty alcohols, fatty acids, fatty amines can be used. Suitable ethoxylated surfactants for use in the compositions, articles, and method of present invention is given in WO 99/55953 published Nov. 4, 1999 to Trinh et al., said publication is incorporated herein by reference.

Other useful surfactants are those having a hydrophobic moiety and hydrophilic ionic groups, including, e.g., anionic, cationic, and amphoteric groups. Examples of suitable nonionic, anionic, cationic, ampholytic, zwitterionic and semipolar nonionic surfactants are disclosed in U.S. Pat. Nos. 5,707,950 and 5,576,282, incorporated herein by reference.

(E) Antimicrobial Active

Optionally, the fabric softening composition of the present invention comprise an effective amount, to kill, or reduce the growth of microbes, of antimicrobial active; preferably from about 0.001% to about 0.8%, more preferably from about 0.002% to about 0.3%, even more preferably from about 0.003% to about 0.2%, by weight of the usage composition. The effective antimicrobial active can function as disinfectants/sanitizers, and is useful in providing protection against organisms that become attached to the fabrics.

Nonlimiting examples of antimicrobial actives which are useful in the present invention are given in WO 99/55953 published Nov. 4, 1999 to Trinh et al., said publication is incorporated herein by reference.

(F) Aminocarboxylate Chelator

Chelators, e.g., ethylenediaminetetraacetic acid (EDTA), hydroxyethylene-diaminetriacetic acid, diethylenetriaminepentaacetic acid, and other aminocarboxylate chelators, and mixtures thereof, and their salts, and mixtures thereof, can optionally be used to increase antimicrobial and preservative effectiveness against Gram-negative bacteria, especially *Pseudomonas* species. Nonlimiting examples of suitable aminocarboxylate chelators and information of their usage are given in U.S. Pat. No. 6,001,343 cited hereinabove, and incorporated herein by reference.

The optional chelators are present in the compositions of this invention at levels of, typically, from about 0.001% to about 0.3%, more preferably from about 0.01% to about 0.1%, most preferably from about 0.02% to about 0.05% by weight of the usage compositions to provide antimicrobial efficacy in this invention.

(G) Odor Control Agent

Fabric softening compositions of the present invention can optionally contain odor control agent, preferably uncomplexed cyclodextrins, water soluble zinc salts, soluble carbonate and/or bicarbonate salts, water soluble ionic polymers, and mixtures thereof. Nonlimiting examples of preferred odor control agents are given in U.S. Pat. No. 5,997,759, issued Dec. 7, 1999 to Trinh et al., said patent is incorporated herein by reference. Typical levels of odor control agent in compositions for usage conditions are from about 0.01% to about 5%, preferably from about 0.1% to about 4%, more preferably from about 0.2% to about 3%, and even more preferably from about 0.3% to about 2%, by weight of the composition.

(a) Cyclodextrin

Suitable cyclodextrin for use in the compositions, articles, and method of present invention is given in WO 99/55953 published Nov. 4, 1999 to Trinh et al., said publication is incorporated herein by reference. Typical levels of cyclodextrin in usage compositions for usage conditions are from about 0.01% to about 5%, preferably from about 0.1% to about 4%, more preferably from about 0.2% to about 3%, and even more preferably from about 0.3% to about 2%, by weight of the composition. It is preferable that the treated fabric contains a level of less than about 5 mg of cyclodextrin per gram of fabric, more preferably less than about 2 mg of cyclodextrin per gram of fabric.

Low Molecular Weight Polyols

Some low molecular weight polyols with relatively high boiling points, as compared to water, are preferred optional ingredients for improving odor control performance of the composition of the present invention when cyclodextrin is present. The mechanism of odor control of low MW polyols, and preferred levels of said polyols, are discussed in U.S. Pat. No. 5,997,759 cited hereinabove, and incorporated herein by reference. Preferably the glycol used is ethylene glycol, propylene glycol, diethylene glycol, dipropylene glycol or mixtures thereof, more preferably ethylene glycol and/or propylene glycol. Cyclodextrins prepared by processes that result in a level of such polyols are highly desirable, since they can be used without removal of the polyols.

(b) Metal Salts

Optionally, but preferably, the present invention can include metallic salts for odor control and/or antimicrobial benefits. The metallic salts are selected from the group consisting of copper salts, zinc salts, and mixtures thereof. These benefits and other benefits are given in U.S. Pat. No. 5,997,759 cited hereinabove, and incorporated herein by reference. Preferably the metallic salts are water-soluble zinc salts, copper salts or mixtures thereof, and more preferably zinc salts, especially $ZnCl_2$.

When metallic salts are added to the composition of the present invention they are typically present at a level of from about 0.1% to about 10%, preferably from about 0.2% to about 8%, more preferably from about 0.3% to about 5% by weight of the usage composition. When zinc salts are used as the metallic salt, and a clear solution is desired, it is preferable that the pH of the solution is adjusted to less than about 7, more preferably less than about 6, most preferably, less than about 5, in order to keep the solution clear.

(c) Soluble Carbonate and/or Bicarbonate Salts

Water-soluble alkali metal carbonate and/or bicarbonate salts, such as sodium bicarbonate, potassium bicarbonate, potassium carbonate, cesium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention it is preferably that incompatible metal salts not be present in the invention. Preferably, when these salts are used the composition should be essentially free of zinc and other incompatible metal ions, e.g., Ca, Fe, Ba, etc. which form water-insoluble salts.

(d) Water-Soluble Ionic Polymers

Some water-soluble polymers, e.g., water-soluble cationic polymer and water-soluble anionic polymers can be used in the composition of the present invention to provide additional odor control benefits. Nonlimiting examples of such polymers that are useful in the present invention are given in U.S. Pat. No. 5,997,759 cited hereinabove, and incorporated herein by reference.

Water-soluble anionic polymers, e.g., polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

When a water-soluble polymer is used it is typically present at a level of from about 0.001% to about 3%, preferably from about 0.005% to about 2%, more preferably from about 0.01% to about 1%, and even more preferably from about 0.05% to about 0.5%, by weight of the usage composition.

(e) Mixtures Thereof

Mixtures of the above materials are desirable, especially when the mixture provides control over a broader range of odors.

(H) Preservative

Optionally, solubilized, water-soluble, antimicrobial preservative can be added to the composition of the present invention if the antimicrobial active (E) is not sufficient, or is not present, especially when cyclodextrin and/or polysaccharide molecules are present in the fabric softening compositions.

Suitable antimicrobial preservative for use in the compositions, articles, and method of present invention is given in WO 99/55953 published Nov. 4, 1999 to Trinh et al., said publication is incorporated herein by reference.

Preferred levels of preservative are from about 0.0001% to about 0.5%, more preferably from about 0.0002% to about 0.2%, most preferably from about 0.0003% to about 0.1 %, by weight of the usage composition.

(I) Adjunct Fabric Softening Agents

The composition of the present invention can optionally contain adjunct quaternary ammonium fabric softening agent to provide additional fabric softening benefit. Examples of quaternary ammonium fabric softening actives are disclosed in U.S. Pat. No. 3,861,870, Edwards et al.; U.S. Pat. No. 4,308,151, Cambre; U.S. Pat. No. 3,886,075, Bernardino; U.S. Pat. No. 4,233,164, Davis; U.S. Pat. No. 4,401,578, Verbruggen; U.S. Pat. No. 3,974,076, Wiersema et al.; and U.S. Pat. No. 4,237,016, Rudkin et al.; said patents being incorporated by reference herein. Some preferred quaternary ammonium fabric softening actives are disclosed in U.S. Pat. No: 4,661,269, issued Apr. 28, 1987, to T. Trinh et al; U.S. Pat. No. 5,545,340, issued Aug. 13, 1996, to Wahl et al.; U.S. Pat. No. 5,747,443 issued May 5, 1998 to E. H. Wahl et al; and U.S. Pat. No. 5,830,845 issued Nov. 3, 1998 to T. Trinh et al; all said patents are incorporated herein by reference.

When the adjunct fabric softening agent is used, it is typically present at a level of from about 0.05% to about 3%, preferably from about 0.1% to about 2%, more preferably from about 0.3% to about 1%, by weight of the usage composition.

(J) Aqueous Carrier

The preferred carrier of the present invention is water. The water which is used can be distilled, deionized, or tap water. Water is the main liquid carrier due to its low cost, availability, safety, and environmental compatibility.

Water is also very useful for fabric wrinkle removal or reduction. Not to be bound by theory, it is believed that water breaks many intrafiber and interfiber hydrogen bonds that keep the fabric in a wrinkle state. It also swells, lubricates and relaxes the fibers to help the wrinkle removal process.

The level of liquid carrier in the compositions of the present invention is typically greater than about 80%, preferably greater than about 90%, more preferably greater than about 95%, by weight of the composition.

Optionally, in addition to water, the carrier can contain a low molecular weight organic solvent that is highly soluble in water, e.g., ethanol, propanol, isopropanol, and the like, and mixtures thereof. Low molecular weight alcohols can help the treated fabric to dry faster. The optional solvent is also useful in the solubilization of some shape retention polymers described hereinbefore. The optional water soluble low molecular weight solvent can be used at a level of up to about 50%, typically from about 1% to about 20%, preferably from about 2% to about 15%, more preferably from about 5% to about 10%, by weight of the total composition. Factors that need to consider when a high level of solvent is used in the composition are odor, flammability, and environment impact; in such cases the optional water soluble low molecular weight solvent can be preferably used at a level of up to about 5%.

(K) Other Optional Ingredients

The composition of the present invention can optionally antistatic agents, insect and moth repelling agents, colorants, especially bluing agents, chemical stabilizers including antioxidants, anti-clogging agents, suds suppressors, brighteners, soil release agents, and mixtures thereof. Suitable optional ingredients for use in the compositions, articles, and method of present invention is given in WO 99/55953 published Nov. 4, 1999 to Trinh et al., said publication is incorporated herein by reference. The total level of optional ingredients is low, preferably less than about 5%, more preferably less than about 3%, and even more preferably less than about 2%, by weight of the usage composition. These optional ingredients exclude the other ingredients specifically mentioned hereinbefore.

II. Article of Manufacture

The fabric softening composition of the present invention can also be used in an article of manufacture comprising said composition plus a spray dispenser. The present invention also relates to an article of manufacture comprising the fabric softening composition in a package, in association with instructions for how to use the composition to treat fabrics correctly, in order to obtain the desirable fabric fabric softening and other optional fabric care results, viz, wrinkle removal and/or reduction, wrinkle resistance, fiber strengthening/anti-wear, fabric wear reduction, fabric color maintenance, fabric color restoration, fabric color fading reduction, soiling prevention and/or reduction, and/or fabric shape retention, and mixtures thereof. A preferred article of manufacture comprises said composition in a spray dispenser, in association with instructions for how to use the composition to treat fabrics correctly, including, e.g., the manner and/or amount of composition to spray, as will be described with more detailed herein below. The instructions for use can also direct the consumer to apply the composition to the fabric in combination with stretching and/or smoothing of fabric, to provide effective fabric softening and/or wrinkle removal. It is important that the instructions be simple and clear, such that using text, pictures and/or icons may be desirable. Said instructions may include instructions that direct the consumer to apply the composition to fabric in the manner and in amounts as describe hereinafter.

The present invention also relates to an article of manufacture comprising a concentrated fabric softening composition comprising polyalkyleneoxy polysiloxane at a level of from about 1% to about 40%, by weight of the concentrated composition, in a package, in association with instructions for how to dilute said concentrated composition to form compositions with the usage concentrations of polyethyleneoxy polysiloxane of, e.g., from about 0.1% to about 5%, by weight of the diluted composition.

Spray Dispenser

The article of manufacture herein comprises a spray dispenser. The fabric softening composition is placed into a spray dispenser in order to be distributed onto the fabric. Said spray dispenser for producing a spray of liquid droplets can be any of the manually activated means as is known in the art, e.g. trigger sprayer, pump sprayer, non-aerosol self-pressurized sprayer, and aerosol-type sprayer, for treating fabric softening composition to small fabric surface areas and/or small number of fabric articles, as well as non-manually operated, powered sprayers for conveniently treating the odor-absorbing composition to large fabric surface areas and/or a large number of garments and/or articles. The spray dispenser herein does not normally include those that will substantially foam the aqueous fabric softening composition. To efficiently provide softness performance it is preferable to treat fabrics with the fabric softening composition in the form of small droplet particles. Desirably, the Sauter mean particle diameter is from about 10μm to about 120 μm, more preferably, from about 20 μm to about 100 μm.

The manually activated spray dispensers include, but are not limited to, aerosol dispenser; self-pressurized non-aerosol container having a convoluted liner and an elastomeric sleeve; non-aerosol, manually activated, pump-spray dispenser; and manually activated trigger-spray dispenser. Non-manually operated spray dispensers include, but are not limited to, powered sprayers, air aspirated sprayers, liquid aspirated sprayers, electrostatic sprayers, and nebulizer sprayers. Detailed descriptions of spray dispensers that are suitable for use in the present invention are given in U.S. Pat. No. 6,001,343, incorporated hereinbefore by reference.

The preferred trigger sprayers are the blue inserted Guala® sprayer, available from Berry Plastics Corp., or the Calmar TS800-1A®, TS1300®, and TS-800-2®, available from Calmar Inc., because of the fine uniform spray characteristics, spray volume, and pattern size. More preferred are sprayers with precompression features and finer spray characteristics and even distribution, such as Yoshino sprayers from Japan. Any suitable bottle or container can be used with the trigger sprayer, the preferred bottle is a 17 fl-oz. bottle (about 500 ml) of good ergonomics similar in shape to the Cinch® bottle. It can be made of any materials such as high density polyethylene, polypropylene, polyvinyl chloride, polystyrene, polyethylene terephthalate, glass, or any other material that forms bottles. Preferably, it is made of high density polyethylene or clear polyethylene terephthalate.

For smaller fluid ounce sizes (such as 1 to 8 ounces), a finger pump can be used with canister or cylindrical bottle. The preferred pump for this application is the cylindrical Euromist II® from Seaquest Dispensing. More preferred are those with precompression features.

III. Method of use

The fabric softening composition of the present invention can be used by distributing, e.g., by placing, an effective amount of the aqueous solution onto the fabric article to be treated. Distribution can be achieved by using a spray device, a roller, a pad, etc., preferably a spray dispenser. For fabric softening, an effective amount, as defined herein, means an amount sufficient to make the fabric feels softer than the fabric treated with water alone. Preferably, the amount of solution is not so much as to saturate or create a pool of liquid on said fabric article or surface and so that when dry there is no visual deposit readily discernible.

An effective amount of the liquid composition of the present invention is preferably sprayed onto fabrics, particularly clothing. The composition can be applied to dry or wet fabrics, preferably dry fabrics. The composition can also be applied onto fabrics in the drying step of a laundry process. When the composition is sprayed onto fabric, an effective amount should be deposited onto the fabric, with the fabric becoming damp or totally saturated with the composition, typically from about 5% to about 150%, preferably from about 10% to about 100%, more preferably from about 20% to about 75%, by weight of the dry fabric. The amount of polyalkyleneoxy polysiloxane fabric softening active typically sprayed onto the fabric is from about 0.005% to about 5%, preferably from about 0.01% to about 2%, more preferably from about 0.03% to about 1%, and even more preferably from about 0.1% to about 1%, by weight of the dry fabric. It is highly preferable to use the preferred particles sizes described hereinbefore, since the areas that receive too much liquid will be slow to dry. Once the fabric has been sprayed, it is air dried or dried in an automatic clothes dryer.

The fabric softening composition can be applied to fabrics made of fibers selected from the group consisting of natural fibers, synthetic fibers, and mixtures thereof; preferably fibers selected from the group consisting of: cellulosic fibers, proteinaceous fibers; synthetic fibers; long vegetable fibers; and mixtures thereof; more preferably selected from the group consisting of cotton, rayon, linen, Tencel, silk, wool and related mammalian fibers, polyester, acrylic, nylon, jute, flax, ramie, coir, kapok, sisal, henequen, abaca, hemp, sunn, and mixtures thereof; and even more preferably selected from the group consisting of cotton, rayon, linen, polyester/cotton blends, silk, wool, polyester, acrylic, nylon, and mixtures thereof. The composition is particularly effective on fabrics made of cotton and cotton blends.

In a still further process aspect of the invention, the composition can be sprayed onto fabrics by in an in-home de-wrinkling chamber containing the fabric to be softened, thereby providing ease of operation. Conventional personal as well as industrial deodorizing and/or de-wrinkling apparatuses are suitable for use herein. Examples of home dewrinkling chambers include shower stalls. The spraying of the composition or compounds onto the fabrics can then occur within the chamber of the apparatus or before placing the fabrics into the chamber. Again, the spraying means should preferably be capable of providing droplets with a weight average diameter of from about 8 to about 100 μm, preferably from about 10 to about 50 μm. Preferably, the loading of moisture on fabrics made of natural and synthetic fibers is from about 5 to about 40%, more preferably from about 5 to about 20% by weight of the dried fabric.

The present invention encompasses the method of spraying a mist of an effective amount of fabric softening solution onto fabric and/or fabric articles. Preferably, said fabric and/or fabric articles include, but are not limited to, clothes, upholstered furniture, carpeting, bed linens, bath linens, tablecloths, sleeping bags, etc.

Textile fabrics can be treated in the mills with compositions containing the various softener actives described herein to provide the desired initial fabric feel and antistatic property. Such compositions to be used in the mills are not typically provided with elements that are important for home use, such as perfume and or detailed instructions for home use that are useful to the consumer. The preferred compositions herein comprise perfume and are suitable for home use, such as spraying fabrics outside of a conventional laundry process.

In situations where one, or very few, fabric items require cleaning, the items are usually washed by hand and line dried. The hand-washed and line-dried fabric items usually feel coarse and harsh, unlike the items that are machine washed and dried in an automatic clothes dryer. Sometimes the hand-washed, line-dried fabric roughness may be remedied by ironing with steam and/or with an ironing spray solution that may smooth out the fabric surface. The compositions herein, however, are capable of providing fabric softness in such situations without the need for an ironing step (e.g. just by spraying the composition onto the fabric item).

A relatively concentrated composition can also be applied directly on wet fabrics, e.g., fabrics that have been just washed and not yet dried, so that the polyethyleneoxy polysiloxane can be diluted in situ on the wet fabrics. Compositions for use to apply on wet fabrics typically comprises polyethyleneoxy polysiloxane at a level of from about 0.1% to about 20%, preferably from about 0.2% to about 5%, and more preferably from about 0.3% to about 3%, by weight of the composition.

All percentages, ratios, and parts herein, in the Specification, Examples, and Claims are by weight and are the normal approximations unless otherwise stated.

The following are non-limiting examples of the instant composition. Perfume compositions that are used herein are as follows:

| Perfume<br>Perfume Ingredients | A<br>Wt. % | B<br>Wt. % | C<br>Wt. % |
|---|---|---|---|
| Anisic aldehyde | — | — | 2 |
| Benzophenone | 3 | 5 | — |
| Benzyl acetate | 10 | 15 | 5 |
| Benzyl salicylate | 5 | 20 | 5 |
| Cedrol | 2 | — | — |
| Citronellol | 10 | — | 5 |
| Coumarin | — | — | 5 |
| Cymal | — | — | 3 |
| Dihydromyrcenol | 10 | — | 5 |
| Flor acetate | 5 | — | 5 |
| Galaxolide | 10 | — | — |
| Lilial | 10 | 15 | 20 |
| Linalyl acetate | 4 | — | 5 |
| Linalool | 6 | 15 | 5 |
| Methyl dihydrojasmonate | 3 | 10 | 5 |
| Phenyl ethyl acetate | 2 | 5 | 1 |
| Phenyl ethyl alcohol | 15 | 10 | 20 |
| alpha-Terpineol | 5 | — | 8 |
| Vanillin | — | — | 1 |
| Total | 100 | 100 | 100 |

| Perfume<br>Perfume Material | D<br>Wt. % | E<br>Wt. % |
|---|---|---|
| Amyl salicylate | 8 | — |
| Benzyl acetate | 8 | 8 |
| Benzyl Salicylate | — | 2 |
| Citronellol | 7 | 27 |
| Dihydromyrcenol | 2 | — |
| Eugenol | 4 | — |
| Flor acetate | 8 | — |
| Galaxolide | 1 | — |
| Geraniol | 5 | — |
| Hexyl cinnamic aldehyde | 2 | — |
| Hydroxycitronellal | 3 | — |
| Lilial | 2 | — |
| Linalool | 12 | 13 |
| Linalyl acetate | 5 | — |
| Lyral | 3 | — |
| Methyl dihydro jasmonate | 3 | — |

-continued

| | | |
|---|---|---|
| Nerol | 2 | — |
| Phenoxy ethyl propionate | — | 3 |
| Phenylethyl acetate | 5 | 17 |
| Phenylethyl alcohol | 8 | 17 |
| alpha-Terpineol | 5 | 13 |
| alpha-Terpinene | 5 | — |
| Tetrahydromyrcenol | 2 | — |
| Total | 100 | 100 |

| Perfume Ingredients | Wt. % |
|---|---|
| Perfume F | |
| Benzophenone | 0.50 |
| Benzyl acetate | 3.00 |
| Benzyl propionate | 1.00 |
| beta gamma Hexenol | 0.20 |
| Cetalox | 0.10 |
| cis 3 Hexenyl acetate | 0.15 |
| cis Jasmone | 0.10 |
| cis-3-Hexenyl salicylate | 1.00 |
| Citral | 0.50 |
| Citronellal nitrile | 0.70 |
| Citronellol | 3.65 |
| Coumarin | 0.70 |
| Cyclal C | 0.30 |
| Cyclo galbanate | 0.40 |
| beta Damascone | 0.05 |
| Dihydro myrcenol | 1.00 |
| Ebanol | 0.50 |
| Flor acetate | 5.00 |
| Florhydral | 0.70 |
| Fructone | 8.50 |
| Frutene | 3.00 |
| Geranyl nitrile | 0.40 |
| Heliotropin | 0.70 |
| Hydroxycitronellal | 2.50 |
| Linalool | 2.00 |
| Linalyl acetate | 1.50 |
| Methyl dihydro jasmonate | 5.00 |
| Methyl heptine carbonate | 0.05 |
| Methyl iso butenyl tetrahydro pyran | 0.15 |
| Methyl phenyl carbinyl acetate | 0.50 |
| Nonalactone | 1.50 |
| P. T. Bucinal | 8.40 |
| para Hydroxy phenyl butanone | 1.30 |
| Phenoxy ethanol | 28.55 |
| Phenyl ethyl acetate | 0.80 |
| Phenyl ethyl alcohol | 10.00 |
| Prenyl acetate | 1.50 |
| Terpineol | 1.50 |
| Verdox | 2.10 |
| Vanillin | 0.50 |
| Total | 100.00 |
| Perfume G | |
| Anisic aldehyde | 2.80 |
| Benzyl acetone | 1.00 |
| cis 3 Hexenyl acetate | 0.30 |
| Citronellal nitrile | 1.30 |
| Citronellol | 6.90 |
| Coumarin | 1.30 |
| Cyclal C | 0.30 |
| Cyclo galbanate | 0.70 |
| Cymal | 1.05 |
| delta Damascone | 0.05 |
| Dihydro myrcenol | 1.30 |
| Dipropylene glycol | 10.20 |
| Dodecalactone | 0.50 |
| Ebanol | 0.10 |
| Ethyl vanillin | 0.10 |
| Flor acetate | 8.00 |
| Florhydral | 1.30 |
| Fructone | 6.00 |
| Galaxolide (50% in isopropyl myristate) | 4.00 |
| gamma Methyl ionone | 1.00 |
| Geranyl nitrile | 0.30 |

-continued

| | |
|---|---|
| Helional | 1.50 |
| Hydroxycitronellal | 2.00 |
| Iso bornyl acetate | 1.80 |
| Ligustral | 0.10 |
| Linalool | 2.50 |
| Methyl dihydro jasmonate | 6.20 |
| Methyl heptine carbonate | 0.10 |
| Methyl iso butenyl tetrahydro pyran | 0.30 |
| Methyl phenyl carbinyl acetate | 1.00 |
| Orange terpenes | 2.00 |
| P. T. Bucinal | 10.00 |
| Phenyl ethyl alcohol | 20.00 |
| Prenyl acetate | 1.50 |
| Verdox | 2.50 |
| Total | 100.00 |

| Perfume Perfume Material | H Wt. % | I Wt. % |
|---|---|---|
| Ambrettolide | 17.0 | 20.0 |
| Ambroxan | 0.5 | 3.0 |
| Aurantiol | 2.0 | 2.0 |
| 1-Cyclohexadecenone | 1.0 | 1.0 |
| Ebanol | 0.5 | 1.0 |
| Ethylene brassylate | 7.0 | 4.0 |
| Hexyl cinnamic aldehyde | 4.0 | 10.0 |
| Hydroxyambran | 0.5 | 0.5 |
| Indolene 50% | 0.5 | 0.5 |
| Gamma methyl ionone | 1.0 | 1.0 |
| Iso E Super | 5.0 | 5.0 |
| Tonalid | 5.0 | 5.0 |
| Okoumal | 24.0 | 15.0 |
| Vetivert acetate | 3.0 | 3.0 |
| 4-Tertiary butyl cyclohexyl acetate | 6.0 | 6.0 |
| Alpha damascone | 1.0 | 1.0 |
| Citronellal nitrile | 2.0 | 2.0 |
| Alpha ionone | 4.0 | 4.0 |
| Frutene | 8.0 | 8.0 |
| Verdox | 8.0 | 8.0 |
| Total | 100.0 | 100.0 |

Perfumes H and I comprise about 80% of substantive perfume ingredients.

The following non-limiting fabric care compositions are prepared by mixing and dissolving the ingredients into clear or translucent solutions, in accord with the present invention:

EXAMPLES I

| | Examples | | | | |
|---|---|---|---|---|---|
| Ingredients | Ia Wt % | Ib Wt % | Ic Wt % | Id Wt % | Ie Wt % |
| Silwet L-7001[a] | 1.4 | — | — | — | — |
| Silwet L-7002 | — | 1.0 | — | — | — |
| Silwet L-7087 | — | — | 1.0 | — | — |
| Silwet L-7200 | — | — | — | 1.3 | — |
| Silwet I-7230 | — | — | — | — | 1.0 |
| Substantive Perfume[b] | 0.1 | 0.1 | 0.04 | 0.05 | 0.1 |
| Kathon | 3 ppm | 3 ppm | 3 ppm | 3 ppm | 3 ppm |
| Distilled water | Bal. | Bal. | Bal. | Bal. | Bal. |

[a]75% active.
[b]Containing at least about 25% of substantive perfume ingredients, by weight of the total perfume composition.

EXAMPLES II

| | Examples | | | | | |
|---|---|---|---|---|---|---|
| Ingredients | IIa Wt % | IIb Wt % | IIc Wt % | IId Wt % | IIe Wt % | IIf Wt % |
| DC 190 | 1.2 | — | — | — | — | — |
| DC 2 5093 | — | 1.0 | — | — | — | — |
| DC 2 5573 | — | — | 1.0 | — | — | — |
| DC 5247 | — | — | — | 1.3 | — | — |
| DC Q2 5220 | — | — | — | — | 1.0 | — |
| Tegopren 5863[a] | — | — | — | — | — | 1.0 |
| Substantive Perfume[b] | 0.1 | 0.1 | 0.04 | 0.05 | 0.1 | 0.04 |
| Kathon | 3 ppm | 3 ppm | 3 ppm | 3 ppm | 3 ppm | 3 ppm |
| Distilled water | Bal. | Bal. | Bal. | Bal. | Bal. | Bal. |

[a]Available from Goldschmidt Chemical Corporation, Hopewell, Virginia.
[b]Containing at least about 25% of substantive perfume ingredients, by weight of the total perfume composition.

EXAMPLES III

| | Examples | | | |
|---|---|---|---|---|
| Ingredients | IIIa Wt % | IIIb Wt % | IIIc Wt % | IIId Wt % |
| Silwet 7220 | 1.2 | — | — | — |
| Silwet 7602 | — | 1.0 | — | — |
| Silwet 7622 | — | — | 1.0 | — |
| Silwet 7650 | — | — | — | 1.3 |
| Tween 20[a] | 1.2 | 1.0 | 1.0 | 1.3 |
| Substantive Perfume | 0.1 | 0.1 | 0.04 | 0.05 |
| Kathon | 3 ppm | 3 ppm | 3 ppm | 3 ppm |
| Distilled water | Bal. | Bal. | Bal. | Bal. |

[a]A polyoxyethylene (20) sorbitan monolaurate, available from ICI Americas, Inc. Wilmington, Delaware.

EXAMPLES III

| | Examples | | | |
|---|---|---|---|---|
| Ingredients | IIIa Wt % | IIIb Wt % | IIIc Wt % | IIId Wt % |
| Silwet 7220 | 1.2 | — | — | — |
| Silwet 7602 | — | 1.0 | — | — |
| Silwet 7622 | — | — | 1.0 | — |
| Silwet 7650 | — | — | — | 1.3 |
| Tween 20[a] | 1.2 | 1.0 | 1.0 | 1.3 |
| Substantive Perfume | 0.1 | 0.1 | 0.04 | 0.05 |
| Kathon | 3 ppm | 3 ppm | 3 ppm | 3 ppm |
| Distilled water | Bal. | Bal. | Bal. | Bal. |

[a]A polyoxyethylene (20) sorbitan monolaurate, available from ICI Americas, Inc. Wilmington, Delaware.

EXAMPLES IV

| Ingredients | Examples | | | |
|---|---|---|---|---|
| | IVa Wt % | IVb Wt % | IVc Wt % | IVd Wt % |
| Silicone of Example 1 | 1.2 | — | — | — |
| Silicone of Example 5 | — | 1.0 | — | — |
| Silicone of Example 9 | — | — | 1.0 | — |
| Silicone of Example 11 | — | — | — | 1.1 |
| Tween 20 | 1.2 | 1.0 | 1.0 | 1.1 |
| Substantive Perfume | 0.05 | 0.05 | 0.05 | 0.05 |
| Kathon | 3 ppm | 3 ppm | 3 ppm | 3 ppm |
| Distilled water | Bal. | Bal. | Bal. | Bal. |

EXAMPLES V

| Ingredients | Examples | | | |
|---|---|---|---|---|
| | Va Wt % | Vb Wt % | Vc Wt % | Vd Wt % |
| Silicone of Example 15 | 1.2 | — | — | — |
| Silicone of Example 18 | — | 1.0 | — | — |
| Silicone of Example 20 | — | — | 1.0 | — |
| Silicone of Example 25 | — | — | — | 1.1 |
| Tween 20 | 1.2 | 1.0 | 1.0 | 1.1 |
| Perfume | 0.05 | 0.05 | 0.05 | 0.05 |
| Kathon | 3 ppm | 3 ppm | 3 ppm | 3 ppm |
| Distilled water | Bal. | Bal. | Bal. | Bal. |

Concentrated compositions of Examples VI-VIII are diluted with water to obtain usage compositions for, e.g., spraying, soaking and/or dipping fabric articles. They can also be used undiluted to treat fabric as rinse additive compositions.

EXAMPLES VI

| Ingredients | Examples | | | | |
|---|---|---|---|---|---|
| | VIa Wt % | VIb Wt % | VIc Wt % | VId Wt % | VIe Wt % |
| Silwet L-7200 | 10 | — | — | — | — |
| Silwet L-7230 | — | 10 | — | — | — |
| DC 190 | — | — | 5 | — | — |
| DC 2 5573 | — | — | — | 10 | — |
| DC 5247 | — | — | — | — | 5 |
| Tween 20 | 1 | 1 | 1 | 1 | 1 |
| Perfume | 0.5 | 0.5 | 0.4 | 0.5 | 0.3 |
| Kathon | 6 ppm | 6 ppm | 6 ppm | 6 ppm | 6 ppm |
| Distilled water | Bal. | Bal. | Bal. | Bal. | Bal. |

EXAMPLES VII

| Ingredients | Examples | | | |
|---|---|---|---|---|
| | VIIa Wt % | VIIb Wt % | VIIc Wt % | VIId Wt % |
| Silwet L-7001 | 15 | — | — | — |
| Silwet L-7087 | — | 10 | — | — |
| Silwet L-7622 | — | — | 5 | — |
| Silwet L-7650 | — | — | — | 10 |
| Tween 20 | 10 | 10 | 5 | 10 |
| Perfume | 0.5 | 0.4 | 0.2 | 0.5 |
| Kathon | 6 ppm | 6 ppm | 6 ppm | 6 ppm |
| Distilled water | Bal. | Bal. | Bal. | Bal. |

EXAMPLES VIII

| Ingredients | Examples | | | |
|---|---|---|---|---|
| | VIIIa Wt % | VIIIb Wt % | VIIIc Wt % | VIIId Wt % |
| Silicone of Example 5 | 10 | — | — | — |
| Silicone of Example 11 | — | 5 | — | — |
| Silicone of Example 15 | — | — | 10 | — |
| Silicone of Example 25 | — | — | — | 15 |
| Tween 20 | 10 | 5 | 10 | 15 |
| Substantive Perfume | 0.5 | 0.3 | 0.4 | 0.7 |
| Kathon | 6 ppm | 6 ppm | 6 ppm | 6 ppm |
| Distilled water | Bal. | Bal. | Bal. | Bal. |

The compositions of Examples I to VIII (diluted when appropriate) are sprayed onto clothing using, e.g., the TS-800 sprayer from Calmar, and allowed to evaporate off of the clothing.

The compositions of Examples I to VIII (diluted when appropriate) are sprayed onto clothing, using a blue inserted Guala® trigger sprayer, available from Berry Plastics Corp. and a cylindrical Euromist II® pump sprayer available from Seaquest Dispensing, respectively, and allowed to evaporate off of the clothing.

The compositions of Examples I to VIII (diluted when appropriate) contained in rechargeable battery-operated Solo Spraystar sprayers are sprayed onto large surfaces of fabric, such as several pieces of clothing, and allowed to evaporate off of these surfaces.

The compositions of Examples I to VIII (diluted when appropriate) are used for soaking or dipping of fabrics which are then optionally wrung or squeezed to remove excess liquid and subsequently dried.

What is claimed is:

1. A method of softening a fabric article in a laundry process, the method comprising:
   a). subjecting a plurality of fabric articles to a laundry process;
   b). selecting at least one of the fabric articles, but not all of the fabric articles;
   c). providing a fabric softening composition comprising a polyalkyleneoxy polysiloxane, perfume, and water, wherein the polyalkyleneoxy polysiloxane is designed with Correlation I:

$$S = 3.246(\sqrt{t\#diSi}) - 1.880(\sqrt{\% Si}) - 0.9066\sqrt{t\#EO} + 17.70 \quad (I)$$

wherein t#diSi is the average total number of the Si(CH$_3$)$_2$O units in the molecule; t#EO is the average total number of the ethyleneoxy CH$_2$CH$_2$O units in the molecule; %Si is the weight percent of all siloxane units in the molecule; and the softness index S is at least 10;

by:
- (i) choosing a desired S value, typically at least about 20;
- (ii) setting a desired average molecular weight, MW, being typically from about 7,500 to about 140,000;
- (iii) setting a desired %EO (weight % of all ethylene EO units in the molecule), then derive t#EO (the average total number of ethyleneoxy EO units in the molecule) with t#EO being typically from about 100 to about 1,800;
- (iv) choosing the type of polyalkyleneoxy polysiloxane selected from the group consisting of: polyethyleneoxy polysiloxane, polyethyleneoxy/polypropyleneoxy polysiloxanes, and mixtures thereof, then setting the desired %Si;
- (v) using the desired values for S, t#EO, and %Si to calculate t#diSi (the approximated total average number of dimethylsiloxane SiMe$_2$O units in the molecule), using Correlation I, where t#diSi is typically from about 40 to about 450;
- (vi) calculating t#Si (the average number of all siloxane groups); and
- (vii) calculating t#linkSi (the average number of the polyalkyleneoxy pendant groups); and d). spraying the selected fabric article(s) with the fabric softening composition from a spray dispenser.

2. The method of claim 1, wherein t#diSi has a value from about 90 to about 510.

3. The method of claim 1, wherein t#EO has a value from about 200 to about 1200.

4. The method of claim 1, wherein %Si has a value from about 3 to about 65.

5. The method of claim 4, wherein %Si has a value from about 12 to about 60.

6. The method of claim 1, wherein the polyalkyleneoxy polysiloxane has a molecular weight of from about 20,000 to about 40,000.

7. The method of claim 1, wherein the polyalkyleneoxy polysiloxane comprises polyethyleneoxy polysiloxane.

8. The method of claim 1, wherein the polyalkyleneoxy polysiloxane comprises polyethyleneoxy/polypropyleneoxy polysiloxane.

9. The method of claim 1, wherein the polyalkyleneoxy polysiloxane is present at a level from about 0.01% to about 10% by weight of the composition.

10. The method of claim 1, wherein the fabric softening composition further comprises a wrinkle control agent, wherein the wrinkle control agent is selected from the group consisting of: a fabric lubricant, shape retention polymer, fabric care polysaccharide, hydrophilic plasticizer, and combinations thereof.

11. The method of clam 10, wherein the wrinkle control agent is present at a level of from about 0.05% to about 5%.

12. The method of claim 1, wherein the perfume is present at a level of from about 0.03% to about 0.05% by weight of the composition and wherein the perfume comprises at least about 25% by weight of the perfume composition of substantive perfume ingredients that have a boiling point of at least about 250° C.

13. The method of claim 1, wherein the fabric softening composition further comprises a surfactant, wherein the surfactant is present at a level of from about 0.05% to about 5% by weight of the composition.

14. The method of claim 13, wherein the surfactant comprises a nonionic surfactant and is present at a polyalkyleneoxy polysiloxane:nonionic surfactant weight ratio of from about 4:1 to about 1:3.

15. The method of claim 1, wherein the fabric softening composition further comprises an antimicrobial active, wherein the antimicrobial active is present at a level of from about 0.001% to about 0.8% by weight of the composition.

16. The method of claim 1, wherein the fabric softening composition further comprises an odor controlling agent, wherein the odor controlling agent is selected from the group consisting of: uncomplexed cyclodextrins, zinc and copper salts, soluble carbonate and/or bicarbonate salts, water soluble ionic polymers, and mixtures thereof, wherein the odor controlling agent is present at a level of from about 0.01% to about 5% by weight of the composition.

17. The method of claim 1, wherein the fabric softening composition further comprises an adjunct quaternary ammonium fabric softening agent, wherein the adjunct quaternary ammonium fabric softening agent is present at a level of from about 0.05% to about 3% by weight of the composition.

18. The method of claim 1, wherein the polyalkyleneoxy polysiloxane is present at a level from about 1% to about 30% by weight of the fabric softening composition, and the method further comprises dilution of the fabric softening composition prior to spraying.

19. The method of claim 1, wherein the laundry process comprises machine washing and drying.

20. The method of claim 1, wherein the laundry process comprises hand washing and air-drying.

* * * * *